US012784224B2

(12) United States Patent
Marie-Nelly et al.

(10) Patent No.: US 12,784,224 B2
(45) Date of Patent: *Nov. 3, 2026

(54) CELLULAR TIME-SERIES IMAGING, MODELING, AND ANALYSIS SYSTEM

(71) Applicant: Insitro, Inc., South San Francisco, CA (US)

(72) Inventors: Herve Marie-Nelly, San Carlos, CA (US); Jeevaa Velayutham, Selangor (MY); Zachary Phillips, San Francisco, CA (US); Shengjiang Tu, Foster City, CA (US)

(73) Assignee: Insitro, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/391,805

(22) Filed: Nov. 17, 2025

(65) Prior Publication Data

US 2026/0073524 A1 Mar. 12, 2026

Related U.S. Application Data

(63) Continuation of application No. 18/666,672, filed on May 16, 2024.

(Continued)

(51) Int. Cl.
*G06T 7/00* (2017.01)
*G06V 10/762* (2022.01)

(Continued)

(52) U.S. Cl.
CPC .......... *G06T 7/0016* (2013.01); *G06V 10/762* (2022.01); *G06V 20/695* (2022.01);

(Continued)

(58) Field of Classification Search
CPC ......... G06T 7/0016; G06T 2207/10016; G06T 2207/20081; G06T 2207/30024;

(Continued)

(56) References Cited

U.S. PATENT DOCUMENTS 11,531,844 B2 * 12/2022 Bharti .................... G06V 20/69
11,686,721 B2 * 6/2023 Takahashi ............ G06T 7/0014 382/133

(Continued)

OTHER PUBLICATIONS

Liu, P., et al., "Chronic Disease Progression Modeling using Semi-Markov Model with Noisy Observations," IISE Annual Conference, Institute of Industrial and Systems Engineering Research Conference (IISE), 2015, pp. 2933-2942.

(Continued)

*Primary Examiner* — Gregory M Desire
(74) *Attorney, Agent, or Firm* — Weaver Austin Villeneuve & Sampson LLP

(57) ABSTRACT

The present disclosure relates generally to providing a cellular time-series imaging, modeling, and analysis platform, and more specifically to acquiring time-series image data and using various machine learning models to model and analyze subcellular particle movements and changes in cellular positional and morphological characteristics using unsupervised embedding generation. The platform can be applied to evaluate various cellular and subcellular processes by generating summary embeddings of time-series image data that enable analysis of dynamic cellular and subcellular processes over time (e.g., the movement of particles within a cell, neurites on developing neurons, etc.) for enhanced identification of differences between cell states (e.g., between sick and healthy cells) and generation of disease models which can be used to analyze the impact of various therapeutic interventions, among other improvements described throughout.

20 Claims, 10 Drawing Sheets
(5 of 10 Drawing Sheet(s) Filed in Color)

100

Related U.S. Application Data

(60) Provisional application No. 63/467,582, filed on May 18, 2023.

(51) Int. Cl.

| | |
|---|---|
| ***G06V 10/77*** | (2022.01) |
| ***G06V 20/69*** | (2022.01) |
| ***G16H 50/20*** | (2018.01) |
| ***G16H 50/50*** | (2018.01) |

(52) U.S. Cl.
CPC ............. *G16H 50/20* (2018.01); *G16H 50/50* (2018.01); *G06T 2207/10016* (2013.01); *G06T 2207/20081* (2013.01); *G06T 2207/30024* (2013.01); *G06V 10/77* (2022.01); *G06V 20/698* (2022.01)

(58) Field of Classification Search
CPC ...... G16H 50/50; G16H 50/20; G06V 20/695; G06V 10/762; G06V 20/698; G06V 10/77
See application file for complete search history.

(56) References Cited

U.S. PATENT DOCUMENTS

| | | | | |
|---|---|---|---|---|
| 11,748,885 | B2 * | 9/2023 | Zhou | G06T 7/0014 382/133 |
| 12,277,711 | B2 | 4/2025 | Marie-Nelly et al. | |
| 2021/0117729 | A1 * | 4/2021 | Bharti | G06V 20/69 |
| 2021/0192737 | A1 * | 6/2021 | Zhou | G06T 7/285 |
| 2024/0386566 | A1 | 11/2024 | Marie-Nelly et al. | |
| 2024/0395415 | A1 | 11/2024 | Marie-Nelly et al. | |
| 2026/0038121 | A1 | 2/2026 | Marie-Nelly et al. | |

OTHER PUBLICATIONS

Mccomb M C., "Machine Learning-Guided, Biomarker-Enabled Disease Progression Modeling," State University of New York, Dissertations & Theses, Jan. 2020, 24 Pages.

* cited by examiner

Neurons, 60x QPI (Phasics Camera), 100ms / frame sampled every 0.1s

Neurons, 60x QPI (Phasics Camera), 100ms / frame sampled every 1.0s

Red Overlay: Computationally Applied 3D Median Filter + Blob Detection

CELLULAR TIME-SERIES IMAGING, MODELING, AND ANALYSIS SYSTEM

CROSS-REFERENCE TO RELATED APPLICATION

An Application Data Sheet is filed concurrently with this specification as part of the present application. Each application that the present application claims benefit of or priority to as identified in the concurrently filed Application Data Sheet is incorporated by reference herein in their entireties and for all purposes.

FIELD

The present disclosure relates generally to a cellular time-series imaging, modeling, and analysis platform, and more specifically to using machine learning models to analyze time-series image data (e.g., to study subcellular particle movements and changes in cellular positional and morphological characteristics over time).

BACKGROUND

Existing systems and methods for monitoring and analyzing living organisms (e.g., live biological cells) fail to provide an adequate mechanism for analyzing subcellular movements (e.g., the movement of particles within a cell, neurites on developing neurons, etc.). Instead, such subcellular particle movements and changes in cellular positional and morphological characteristics have been considered to be too random, transient, noisy, and/or complex to derive insight from. Accordingly, such information is not studied, for example, in the context of cell monitoring, disease modeling, and drug discovery.

SUMMARY

Disclosed herein are methods, systems, electronic devices, non-transitory storage media, and apparatuses directed generally to providing a cellular time-series imaging, modeling, and analysis platform, and more specifically to acquiring time-series image data and using various machine learning models to model and analyze subcellular particle movements and changes in cellular positional and morphological characteristics over time. The platform can be applied to study various cellular and subcellular processes.

Recently, the assignee herein developed systems and methods for autonomous cell imaging and modeling. Such a system is described, for example in U.S. patent application Ser. No. 18/111,405 and PCT Application No. PCT/US2022/080200, both of which are incorporated herein by reference in their entirety. The cellular time-series imaging, modeling, and analysis platform described herein provides numerous practical applications related to the studying and control of cellular and subcellular processes using time-series image data. In some embodiments, the cellular time-series imaging, modeling, and analysis platform can be used to acquire time-series image data and generate summary embeddings that provide a lower-dimensional representation of the time-series image data for downstream analysis. Embeddings capture rich semantic information of imaging data (e.g., features of the microscopic structure of tissues reflected in the image, including cellular substructures), while excluding information that is not relevant to downstream analyses (e.g., orientation of the image). Further, a summary embedding of time-series image data (e.g., determined based on a sequence of embeddings as described herein) captures a time-dimension, and allows for analysis of dynamic cellular processes over time. Summary embeddings thus enable analysis of subcellular movements (e.g., the movement of particles within a cell, neurites on developing neurons, etc.) and identification of differences between cell states (e.g., differences in subcellular movements between sick and healthy cells). Summary embeddings can also be used to generate disease models which enhance analysis of the impact of various therapeutic interventions.

Time-series image data may include a set of images of the same region of interest (e.g., a cell, a part of a cell), ordered chronologically. The time-series image data can include a burst of images or a video segment and can be encoded by one or more machine learning models as a sequence of embeddings, which can in turn be encoded as a summary embedding having a temporal dimension based on temporal information associated with the sequence of embeddings, as described throughout. In some embodiments, the system can continuously generate time-series image data of a set of live biological cells in a nondestructive way and analyze the images efficiently using machine-learning techniques (e.g., self-supervised machine-learning models) to evaluate the impact of a physical, chemical or genetic perturbation (e.g., a chemical treatment, a therapeutic agent, a genetic modification, a change in media, or any combination thereof) on the cells. In some embodiments, the system can generate time-series image data of different sets of live biological cells corresponding to different disease states, convert the time-series image data to lower-dimensional summary embeddings, and generate a disease model in a topological space, which can be used to model the progression of a disease. In some embodiments, the system can continuously generate time-series image data of a cell culture in a non-destructive way and analyze the time-series image data to study a characteristic of interest of the cell culture such as the cell proliferation rate, reversion to a healthy phenotype, etc.

In some embodiments, the cellular time-series imaging, modeling, and analysis platform comprises a plurality of stages. In some embodiments, the platform comprises a first autonomous imaging stage. In some embodiments, the first autonomous imaging stage provides label-free time-series imaging (i.e., does not rely on fluorescence dyes to label different cellular components), such as quantitative phase imaging ("QPI"), to acquire one or more sets of time series image data. In some embodiments, the time-series image data include a time series of images. In some embodiments, the time-series image data include a video segment. The imaging stage may acquire a time series of phase images depicting the positional and morphological characteristics in particular cellular substructures. In some embodiments, the imaging stage is compatible with low photo-toxicity fluorescence and autofluorescence multi spectral time-series imaging techniques. The imaging stage may acquire a time series of fluorescence images and/or autofluorescence images of the live biological cells from transformed bright-field images. In some embodiments, the time-series image data of live biological cells (e.g., phase images, fluorescence images, autofluorescence images, etc.) are captured at the imaging stage using a microscope according to an optical setup, which can be manually and/or automatically configured.

In some embodiments, the time-series image data includes a plurality of phase images captured prior to or after a plurality of fluorescence images. Such an acquisition configuration provides a number of technological advantages over acquiring only one of either phase images or fluorescence images. For instance, acquiring both phase and fluorescence time-series image data enables the cross-registration and validation of both phase and immunohistochemistry readouts at the same location (e.g., region of interest of a cell), which may be used as labels to confirm the biological origin of a change in refractive index. In addition, fluorescence channel may be useful as a phenotypic readout in many cases. Time-series image data captured using both fluorescence imaging and phase imaging may be used as data to train a machine learning model, as described further throughout.

In addition, capturing time-series image data comprising a time series of images and/or a video segment provides numerous technical advantages over other imaging techniques. For instance, time-series image data can depict subcellular particle movements, which, to a human observer may appear random, noisy, or transient. By acquiring time series image data depicting such seemingly random movements and processes and inputting the time series images into trained machine learning models, various patterns representative of relationships between movements and cell state, disease progression, and so on, may be identified, which may lead to new discoveries in the treatment of numerous diseases.

In some embodiments, the platform comprises a second, machine-learning based, stage. At the second stage, an exemplary system (e.g., one or more electronic devices performs machine-learning-based image processing on the time-series image data of live biological cells to obtain representations (e.g., embeddings). An embedding is a vector representation of a phenotypic state of the live biological cells. In some embodiments, the exemplary system includes a first trained machine learning model that determines one or more sequences of embeddings based on one or more sets of time-series image data. Each embedding of the one or more sequences of embeddings can represent morphological or positional characteristics of the cell or cellular substructures and/or processes at a particular time point (e.g., a single frame in the set of time-series image data), such that the sequences represent the plurality of morphological or positional characteristics of the cell or cellular substructures and/or processes at a plurality of respective time points. Each embedding of the sequence of embeddings, as described above, captures rich semantic information of the imaging data (e.g., features of the microscopic structure of tissues reflected in the image, including cellular substructures), while excluding information that is not relevant to downstream analyses (e.g., orientation of the image).

In some embodiments, one or more summary embeddings are determined based on the one or more sequences of embeddings. The summary embeddings may be determined by inputting the sequences of embeddings into a second trained machine learning model. In some embodiments, summary embeddings are instead determined directly from sets of time series image data by inputting the sets of time-series image data into a trained machine learning model that can process time-series image data directly (e.g., a model that can directly process video data). The summary embeddings can account for dynamics (e.g., subcellular movements) between subsequent frames in the set of time-series image data. As such, the summary embedding incorporates temporal information of the set of time-series image data.

The combination of time-series image data and machine learning models trained to determine summary embeddings based on the time-series image data can enable increasingly complex modeling and analysis of cellular and subcellular morphologies, movements, and processes that existing systems have failed to provide. The systems and methods described herein can enable users (e.g., researchers) to determine relationships between seemingly random particle movements and structural changes at the cellular and subcellular level and disease states, metabolic states, and/or kinetic states of the observed cells to, for example, gain a better understanding of biological processes and evaluate therapeutic interventions in novel manners.

In some embodiments, the platform may further include a third stage for data analysis. In some embodiments, the summary embeddings generated in the second stage are used for downstream tasks. In some embodiments, the summary embeddings can be used to determine a cell state of the one or more cells. The cell state may be indicative of a diseased state, a healthy state, a degree of the diseased state, a level of metabolic activity, or a kinetic state. In some embodiments, an exemplary system may determine, based on the cell state of the one or more cells and the set of time-series image data, a relationship between one or more time-variant morphological characteristics depicted in the set of time-series image data and the cell state of the one or more cells or a relationship between one or more subcellular or cellular movements or processes depicted in the set of time-series image data and the cell state of the one or more cells. In some embodiments, a human user of the system may compare the cell state to the time series in image data to identify relationships between time-variant morphological characteristics (e.g., subcellular particle movements) in the time-series images and the determined cell state.

In some embodiments, the summary embeddings can be used to determine the impact of a physical, chemical or genetic perturbation (e.g., a chemical treatment, therapeutic agent, a genetic treatment or a change in media, or any combination thereof) in slowing down or reversing the progression of a disease by, for instance, detecting shifts in cell state classification. In some embodiments, the summary embeddings can be used to generate a disease model.

In some embodiments, the disease model can be used to generate synthetic images of one or more disease states of the cells. The synthetic images may be compared to a ground truth image of a cell to determine the accuracy of the disease state model. Further, the synthetic images may be used to study the morphological characteristics of a disease.

Overall, the cellular time-series imaging, modeling, and analysis platform provides an imaging and modeling setup that can be used to analyze subcellular movements and processes at exceedingly short time scales to identify relationships between seemingly random subcellular movements and biological processes (e.g., cell state, the progression and treatment of various diseases).

In some aspects, provided herein is a method for determining a cell state of one or more cells, the method comprising: receiving a set of time-series image data depicting one or more cells; determining a sequence of embeddings by inputting the set of time-series image data into a first trained machine learning model; determining a summary embedding based on the sequence of embeddings, the summary embedding comprising a temporal dimension based on temporal information associated with the sequence of embeddings; and determining the cell state of the one or more cells of the subject by inputting the summary embedding into a second trained machine learning model.

In some embodiments, the temporal information associated with the sequence of embeddings comprises a temporal relationship between a first embedding in the sequence of embeddings and a second embedding in the sequence of embeddings.

In some embodiments, the temporal information associated with the sequence of embeddings comprises a sequential relationship between a first embedding in the sequence of embeddings and a second embedding in the sequence of embeddings.

In some embodiments, the temporal information associated with the sequence of embeddings comprises a time stamp associated with each embedding in the sequence of embeddings.

In some embodiments, the set of time-series image data comprises a time series of images.

In some embodiments, the set of time-series image data comprises a video segment.

In some embodiments, the set of time series image data comprises image data acquired at a frame rate of at least four frames per second or eight frames per second.

In some embodiments, the set of time-series image data comprises a plurality of phase images.

In some embodiments, the plurality of phase images is captured using an imager with a frame rate of at least four frames per second or at least one frame per second. In some embodiments, the frame rate is about 40 frames per second or about 8 frames per second.

In some embodiments, the set of time-series image data comprises a plurality of fluorescence images. In some embodiments, the plurality of fluorescence images is captured using an imager with a frame rate of at least four frames per second or at least one frame per second.

In some embodiments, the cell state is indicative of a diseased state, a healthy state, or a degree of the diseased state.

In some embodiments, the method further comprises: determining, based on the cell state of the one or more cells and the set of time-series image data, a relationship between one or more time-variant morphological characteristics depicted in the set of time-series image data and the cell state of the one or more cells.

In some embodiments, the method further comprises: determining, based on the cell state of the one or more cells and the set of time-series image data, a relationship between one or more subcellular or cellular movements or processes depicted in the set of time-series image data and the cell state of the one or more cells.

In some embodiments, the cell state includes an indication of an accumulation of lipids.

In some embodiments, the cell state is indicative of a level of metabolic activity.

In some embodiments, the cell state is indicative of a kinetic state.

In some embodiments, a rate of change in the cell state is indicative of a variation of a cellular process, wherein the cellular process includes any one or more of a cargo transport, an organelle assembly, and an organelle disassembly.

In some embodiments, the method further comprises mapping a network of one or both of axons and neurites to a cell of the one or more cells based on the set of time-series image data and the cell state of the one or more cells.

In some embodiments, the first trained machine learning model comprises a self-supervised machine learning model.

In some embodiments, the first trained machine learning model is trained using an unlabeled training dataset.

In some embodiments, the unlabeled training dataset comprises a plurality of images of biological samples.

In some embodiments, the first machine learning model is pre-trained using unlabeled images that do not depict biological samples and retrained using unlabeled images of biological samples.

In some embodiments, determining the summary embedding based on the sequence of embeddings comprises: inputting the sequence of embeddings into a third trained machine learning model.

In some embodiments, the third trained machine learning model comprises: a transformer model, a recurrent neural network ("RNN"), a long short-term network ("LSTM"), or any combination thereof.

In some embodiments, the second trained machine learning model comprises a trained classifier.

In some embodiments, the second trained machine learning model comprises a trained regression model.

In some embodiments, the set of time-series image data depicts a single cell. In some embodiments, the single cell is identified using an image segmentation model.

In some embodiments, the one or more cells comprise one or more live biological cells.

In some embodiments, the one or more live biological cells comprise one or more mammalian cells.

In some embodiments, the one or more live biological cells comprise one or more neurons.

In some embodiments, the one or more live biological cells comprise healthy cells, diseased cells, or any combination thereof.

In some embodiments, the one or more live biological cells comprise one or more genetic mutations.

In some embodiments, the one or more genetic mutations is selected from the group consisting of a deletion mutation, insertion mutation, substitution mutation, missense mutation, nonsense mutation, and frameshift mutation.

In some embodiments, the one or more live biological cells have a phenotypic difference compared to healthy cells that do not comprise the one or more genetic mutations.

In some embodiments, the phenotypic difference comprises a difference in metabolic activity, cellular kinetics, cellular morphology, or any combination thereof.

In some aspects, provided herein is a non-transitory computer-readable storage medium storing one or more programs for determining a cell state of one or more cells, the one or more programs comprising instructions, which when executed by one or more processors of an electronic device, cause the electronic device to: receive a set of time-series image data depicting one or more cells; determine a sequence of embeddings by inputting the set of time-series image data into a first trained machine learning model; determine a summary embedding based on the sequence of embeddings, the summary embedding comprising a temporal dimension based on temporal information associated with the sequence of embeddings; and determine the cell state of the one or more cells of the subject by inputting the summary embedding into a second trained machine learning model.

In some aspects, provided herein is a system for determining a cell state of one or more cells, comprising: one or more processors; a memory; and one or more programs, wherein the one or more programs are stored in the memory and configured to be executed by the one or more processors, the one or more programs including instructions for: receiving a set of time-series image data depicting one or more cells; determining a sequence of embeddings by inputting the set of time-series image data into a first trained machine learning model; determining a summary embedding based on the sequence of embeddings, the summary embedding comprising a temporal dimension based on temporal information associated with the sequence of embeddings; and determining the cell state of the one or more cells of the subject by inputting the summary embedding into a second trained machine learning model.

In some aspects, provided herein is a method for modeling a progression of a disease, the method comprising: obtaining a first plurality of sets of time-series image data of a first non-zero concentration of live biological cells expressing a first disease state of the disease; determining a first plurality of sequences of embeddings by inputting the first plurality of sets of time-series image data into a trained machine learning model; determining a first plurality of summary embeddings based on the first plurality of sequences of embeddings, wherein a summary embedding of the first plurality of summary embeddings comprises a temporal dimension based on temporal information associated with a first sequence of embeddings in the first plurality of sequences of embeddings; obtaining a second plurality of sets of time-series image data of a second non-zero concentration of live biological cells expressing a second disease state of the disease; determining a second plurality of sequences of embeddings by inputting the second plurality of sets of time-series image data into the trained machine learning model; determining a second plurality of summary embeddings based on the second plurality of sequences of embeddings, wherein a summary embedding of the second plurality of summary embeddings comprises a temporal dimension based on temporal information associated with a second sequence of embeddings in the second plurality of sequences of embeddings; generating a disease model based on the first plurality of summary embeddings and the second plurality of summary embeddings; and modeling a progression of the disease based on the disease model.

In some embodiments, the temporal information associated with the first sequence of embeddings comprises a temporal relationship between a first embedding in the first sequence of embeddings and a second embedding in the first sequence of embeddings.

In some embodiments, the temporal information associated with the first sequence of embeddings comprises a sequential relationship between a first embedding in the first sequence of embeddings and a second embedding in the first sequence of embeddings.

In some embodiments, the temporal information associated with the first and second sequence of embeddings comprises a time stamp associated with each embedding in the first sequence of embeddings and second sequence of embeddings.

In some embodiments, generating the disease model comprises: mapping the first plurality of summary embeddings and the second plurality of summary embeddings into a topological space.

In some embodiments, the method further comprises: identifying a location of a first cluster of summary embeddings based on the first plurality of summary embeddings in the topological space; generating a representation of the first disease state based on the location of the first cluster; identifying a location of a second cluster of summary embeddings based on the second plurality of summary embeddings in the topological space; and generating a representation of the second disease state based on the location of the second cluster.

In some embodiments, the method further comprises: generating a disease axis based on the location of the first cluster and the location of the second cluster.

In some embodiments, the disease axis represents a hyperplane separating a centroid of the first cluster of summary embeddings from a centroid of the second cluster of summary embeddings.

In some embodiments, the method further comprises: identifying one or more embeddings in the topological space based on the disease axis.

In some embodiments, the method further comprises: generating one or more synthetic images, using a GAN model, based on the identified one or more embeddings.

In some embodiments, the method further comprises: comparing a phenotype depicted in the one or more synthetic images to one or more real images depicting a real cell to validate the phenotype depicted in the one or more synthetic images.

In some embodiments, the phenotype comprises a neurite length, a cell size, a movement of one or more particles within a cell, or any combination thereof.

In some embodiments, the method further comprises: obtaining a first set of time-series image data of one or more diseased live biological cells; determining a first sequence of embeddings by inputting the first set of time-series image data into the trained machine learning model; determining a first summary embedding based on the first sequence of embeddings; applying a perturbation to the one or more diseased live biological cells; after applying the perturbation, obtaining a second set of time-series image data of the one or more diseased live biological cells; determining a second sequence of embeddings by inputting the second set of time-series image data into the trained machine learning model; determining a second summary embedding based on the second sequence of embeddings; and determining, based on the first summary embedding, the second summary embedding, and the disease model, an impact of the perturbation on a reversion of the one or more diseased live biological cells from a diseased state.

In some embodiments, determining the impact of the perturbation comprises: comparing: a location of the first summary embedding in the topological space; a location of the second summary embedding in the topological space; the location of the first cluster; and the location of the second cluster.

In some embodiments, the perturbation is a chemical treatment, a therapeutic agent, a genetic modification, a change in media, or any combination thereof.

In some embodiments, the method further comprises: determining a dosage for the perturbation based on the determination of the impact of the perturbation.

In some embodiments, the method further comprises: determining one or more dose administration intervals for administering the perturbation based on the determination of the impact of the perturbation.

In some embodiments, a set of time-series image data of the first plurality of sets of time-series image data and the second plurality of sets of time-series image data comprises a time series of images.

In some embodiments, a set of time-series image data of the first plurality of sets of time-series image data and the second plurality of sets of time-series image data comprises a video segment.

In some embodiments, a set of time-series image data of the first plurality of sets of time-series image data and the second plurality of sets of time-series image data comprises image data acquired at a frame rate of at least four frames per second or at least eight frames per second.

In some embodiments, a set of time-series image data of the first plurality of sets of time-series image data and the second plurality of sets of time-series image data comprises a plurality of phase images.

In some embodiments, the plurality of phase images is captured using an imager with a frame rate of at least 4 frames per second or at least 1 frame per second.

In some embodiments, the frame rate is about 40 frames per second or 8 frames per second.

In some embodiments, a set of time-series image data of the first plurality of sets of time-series image data and the second plurality of sets of time-series image data comprises a plurality of fluorescence images.

In some embodiments, the plurality of fluorescence images is captured using an imager with a frame rate of at least 4 frames per second or at least 1 frame per second.

In some embodiments, the trained machine learning model comprises a self-supervised machine learning model.

In some embodiments, the trained machine learning model is trained using an unlabeled training dataset.

In some embodiments, the unlabeled training dataset comprises a plurality of images of biological samples.

In some embodiments, the machine learning model is pre-trained using unlabeled images that do not depict biological samples and retrained using unlabeled images of biological samples.

In some embodiments, a set of time-series image data of the first plurality of sets of time-series image data and the second plurality of sets of time-series image data depicts a single cell.

In some embodiments, the single cell is identified using an image segmentation model.

In some embodiments, the live biological cells comprise one or more mammalian cells.

In some embodiments, the live biological cells comprise one or more neurons.

In some aspects, provided herein is a non-transitory computer-readable storage medium storing one or more programs for modeling a progression of a disease, the one or more programs comprising instructions, which when executed by one or more processors of an electronic device, cause the electronic device to: obtain a first plurality of sets of time-series image data of a first non-zero concentration of live biological cells expressing a first disease state of the disease; determine a first plurality of sequences of embeddings by inputting the first plurality of sets of time-series image data into a trained machine learning model; determine a first plurality of summary embeddings based on the first plurality of sequences of embeddings, wherein a summary embedding of the first plurality of summary embeddings comprises a temporal dimension based on temporal information associated with a first sequence of embeddings in the first plurality of sequences of embeddings; obtain a second plurality of sets of time-series image data of a second non-zero concentration of live biological cells expressing a second disease state of the disease; determine a second plurality of sequences of embeddings by inputting the second plurality of sets of time-series image data into the trained machine learning model; determine a second plurality of summary embeddings based on the second plurality of sequences of embeddings, wherein a summary embedding of the second plurality of summary embeddings comprises a temporal dimension based on temporal information associated with a second sequence of embeddings in the second plurality of sequences of embeddings; generate a disease model based on the first plurality of summary embeddings and the second plurality of summary embeddings; and model a progression of the disease based on the disease model.

In some aspects, provided herein is a system for modeling a progression of a disease, comprising: one or more processors; a memory; and one or more programs, wherein the one or more programs are stored in the memory and configured to be executed by the one or more processors, the one or more programs including instructions for: obtaining a first plurality of sets of time-series image data of a first non-zero concentration of live biological cells expressing a first disease state of the disease; determining a first plurality of sequences of embeddings by inputting the first plurality of sets of time-series image data into a trained machine learning model; determining a first plurality of summary embeddings based on the first plurality of sequences of embeddings, wherein a summary embedding of the first plurality of summary embeddings comprises a temporal dimension based on temporal information associated with a first sequence of embeddings in the first plurality of sequences of embeddings; obtaining a second plurality of sets of time-series image data of a second non-zero concentration of live biological cells expressing a second disease state of the disease; determining a second plurality of sequences of embeddings by inputting the second plurality of sets of time-series image data into the trained machine learning model; determining a second plurality of summary embeddings based on the second plurality of sequences of embeddings, wherein a summary embedding of the second plurality of summary embeddings comprises a temporal dimension based on temporal information associated with a second sequence of embeddings in the second plurality of sequences of embeddings; generating a disease model based on the first plurality of summary embeddings and the second plurality of summary embeddings; and modeling a progression of the disease based on the disease model.

BRIEF DESCRIPTION OF THE FIGURES

Various aspects of the disclosure are set forth with particularity in the appended claims. The patent or application file contains at least one drawing executed in color. Copies of this patent or patent application publication with color drawing(s) will be provided by the Office upon request and payment of the necessary fee. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
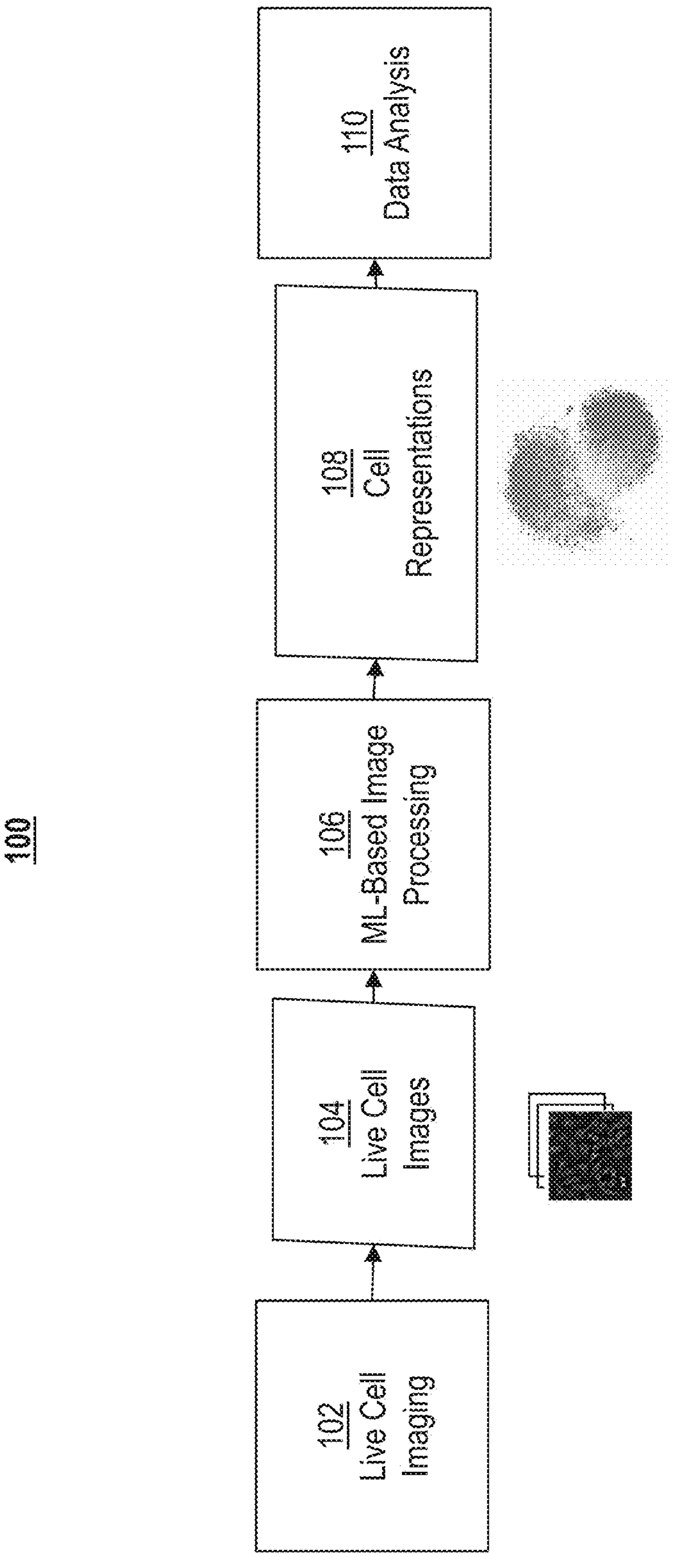
FIG. 1 illustrates a cellular time-series imaging, modeling, and analysis platform, in accordance with some embodiments.

Disclosed herein are methods, systems, electronic devices, non-transitory storage media, and apparatuses directed generally to providing a cellular time-series imaging, modeling, and analysis platform, and more specifically to acquiring time-series image data and using various machine learning models to model and analyze subcellular particle movements, particle accumulation and changes in cellular positional and morphological characteristics over time. The platform can be applied to study various cellular and subcellular processes.

The cellular time-series imaging, modeling, and analysis platform described herein provides numerous practical applications related to the studying and control of cellular and subcellular processes using time-series image data. In some embodiments, the cellular time-series imaging, modeling, and analysis platform can be used to acquire time-series image data and generate summary embeddings that provide a lower-dimensional representation of the time-series image data for downstream analysis. Embeddings capture rich semantic information of imaging data (e.g., features of the microscopic structure of tissues reflected in the image, including cellular substructures), while excluding information that is not relevant to downstream analyses (e.g., orientation of the image). Further, a summary embedding of time-series image data (e.g., determined based on a sequence of embeddings as described herein) captures a time-dimension, and allows for analysis of dynamic cellular processes over time. Summary embeddings thus enable analysis of subcellular movements (e.g., the movement of particles within a cell, neurites on developing neurons, etc.) and identification of differences between cell states (e.g., differences in subcellular movements between sick and healthy cells). Summary embeddings can also be used to generate disease models which enhance analysis of the impact of various cellular perturbations.

Time-series image data may include a set of images of the same region of interest (e.g., a cell, a part of a cell), ordered chronologically. The time-series image data can include a burst of images or a video segment and can be encoded by one or more machine learning models as a sequence of embeddings, which can in turn be encoded as a summary embedding having a temporal dimension, as described throughout. In some embodiments, the system can continuously generate time-series image data of a set of live biological cells in a nondestructive way and analyze the images efficiently using machine-learning techniques (e.g., self-supervised machine-learning models) to evaluate the impact of a physical, chemical or genetic perturbation (e.g., a chemical treatment, a genetic treatment) on the cells. In some embodiments, the system can generate time-series image data of different sets of live biological cells corresponding to different disease states, convert the time-series image data to lower-dimensional summary embeddings, and generate a disease model in a topological space, which can be used to model the progression of a disease. In some embodiments, the system can continuously generate time-series image data of a cell culture in a non-destructive way and analyze the time-series image data to study a characteristic of interest of the cell culture such as the cell proliferation rate, reversion to a healthy phenotype, etc.

In some embodiments, the cellular time-series imaging, modeling, and analysis platform comprises a plurality of stages. In some embodiments, the platform comprises a first autonomous imaging stage. In some embodiments, the first autonomous imaging stage provides label-free time-series imaging (i.e., does not rely on fluorescence dyes to label different cellular components), such as quantitative phase imaging ("QPI"), to acquire one or more sets of time series image data. In some embodiments, the time-series image data include a time series of images. In some embodiments, the time-series image data include a video segment. The imaging stage may acquire a time series of phase images depicting the positional and morphological characteristics in particular cellular substructures. In some embodiments, the imaging stage is compatible with low photo-toxicity fluorescence and autofluorescence multi spectral time-series imaging techniques. The imaging stage may acquire a time series of fluorescence images and/or autofluorescence images of the live biological cells from transformed bright-field images. In some embodiments, the time-series image data of live biological cells (e.g., phase images, fluorescence images, autofluorescence images, etc.) are captured at the imaging stage using a microscope according to an optical setup, which can be manually and/or automatically configured.

In some embodiments, the time-series image data includes a plurality of phase images captured prior to or after a plurality of fluorescence images. Such an acquisition configuration provides a number of technological advantages over acquiring only one of either phase images or fluorescence images. For instance, acquiring both phase and fluorescence time-series image data enables the cross-registration and validation of both phase and immunohistochemistry readouts at the same location (e.g., region of interest of a cell), which may be used as labels to confirm the biological origin of a change in refractive index. In addition, fluorescence channel may be useful as a phenotypic readout in many cases. Time-series image data captured using both fluorescence imaging and phase imaging may be used as data to train a machine learning model, as described further throughout.

In addition, capturing time-series image data comprising a time series of images and/or a video segment provides numerous technical advantages over other imaging techniques. For instance, time-series image data can depict subcellular particle movements, which, to a human observer may appear random, noisy, or transient. By acquiring time series image data depicting such seemingly random movements and processes and inputting the time series images into trained machine learning models, various patterns representative of relationships between movements and cell state, disease progression, and so on, may be identified, which may lead to new discoveries in the treatment of numerous diseases.

In some embodiments, the platform comprises a second, machine-learning based, stage. At the second stage, an exemplary system (e.g., one or more electronic devices performs machine-learning-based image processing on the time-series image data of live biological cells to obtain representations (e.g., embeddings). An embedding is a vector representation of a phenotypic state of the live biological cells. In some embodiments, the exemplary system includes a first trained machine learning model that determines one or more sequences of embeddings based on one or more sets of time-series image data. Each embedding of the one or more sequences of embeddings can represent morphological or positional characteristics of the cell or cellular substructures and/or processes at a particular time point (e.g., a single frame in the set of time-series image data), such that the sequences represent the plurality of morphological or positional characteristics of the cell or cellular substructures and/or processes at a plurality of respective time points. Each embedding of the sequence of embeddings, as described above, captures rich semantic information of the imaging data (e.g., features of the microscopic structure of tissues reflected in the image, including cellular substructures), while excluding information that is not relevant to downstream analyses (e.g., orientation of the image).

In some embodiments, one or more summary embeddings are determined based on the one or more sequences of embeddings. The summary embeddings may be determined by inputting the sequences of embeddings into a second trained machine learning model. In some embodiments, summary embeddings are instead determined directly from sets of time series image data by inputting the sets of time-series image data into a trained machine learning model that can process time-series image data directly (e.g., a model that can directly process video data). The summary embeddings can account for dynamics (e.g., subcellular movements) between subsequent frames in the set of time-series image data. As such, the summary embedding incorporates temporal information of the set of time-series image data.

The combination of time-series image data and machine learning models trained to determine summary embeddings based on the time-series image data can enable increasingly complex modeling and analysis of cellular and subcellular morphologies, movements, and processes that existing systems have failed to provide. The systems and methods described herein can enable users (e.g., researchers) to determine relationships between seemingly random particle movements and structural changes at the cellular and subcellular level and disease states, metabolic states, and/or kinetic states of the observed cells to, for example, gain a better understanding of biological processes and evaluate therapeutic interventions in novel manners.

In some embodiments, the platform may further include a third stage for data analysis. In some embodiments, the summary embeddings generated in the second stage are used for downstream tasks. In some embodiments, the summary embeddings can be used to determine a cell state of the one or more cells. The cell state may be indicative of a diseased state, a healthy state, a degree of the diseased state, a level of metabolic activity, or a kinetic state. In some embodiments, an exemplary system may determine, based on the cell state of the one or more cells and the set of time-series image data, a relationship between one or more time-variant morphological characteristics depicted in the set of time-series image data and the cell state of the one or more cells or a relationship between one or more subcellular or cellular movements or processes depicted in the set of time-series image data and the cell state of the one or more cells. In some embodiments, a human user of the system may compare the cell state to the time series image data to identify relationships between time-variant morphological characteristics (e.g., subcellular particle movements) in the time-series images and the determined cell state.

In some embodiments, the summary embeddings can be used to determine the impact of a physical, chemical or genetic perturbation (e.g., a chemical treatment, a therapeutic agent, a genetic treatment or a change in media, or any combination thereof) in slowing down or reversing the progression of a disease by, for instance, detecting shifts in cell state classification. In some embodiments, the summary embeddings can be used to generate a disease model.

In some embodiments, the disease model can be used to generate synthetic images of one or more disease states of the cells. The synthetic images may be compared to a ground truth image of a cell to determine the accuracy of the disease state model. Further, the synthetic images may be used to study the morphological characteristics of a disease.

Overall, the cellular time-series imaging, modeling, and analysis platform provides an imaging and modeling setup that can be used to analyze subcellular movements and processes at exceedingly short time scales to identify relationships between seemingly random subcellular movements and biological processes (e.g., cell state, the progression and treatment of various diseases).

FIG. 1 illustrates an exemplary autonomous cell imaging and modeling system, in accordance with some embodiments. Process 100 is performed, for example, at least partially using one or more electronic devices. While portions of process 100 are described herein as being performed by particular devices, it will be appreciated that process 100 is not so limited. In process 100, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

At block 102, the system obtains time series image data 104 of live biological cells (e.g., in vitro cell cultures) using techniques that do not destroy the imaged live biological cells. Further, the time-series images in the time-series image data enable visualization, modeling, and analysis of subcellular movements and processes over miniscule time ranges (e.g., at frame rates of at least four frames per second, at frame rates of at least eight frames per second).

The live biological cells may be mammalian cells. In some embodiments, the cells are healthy cells. In some embodiments, the healthy cells have not been previously treated (e.g., with a perturbation (such as, a chemical treatment, a therapeutic agent, a genetic modification, a change in media, or any combination thereof). In some embodiments, the healthy cells have been previously treated with a perturbation. In some embodiments, the cells are diseased cells. In some embodiments, the diseased cells have not been previously treated (e.g., with a perturbation (such as, a chemical treatment, a therapeutic agent, a genetic modification, a change in media, or any combination thereof). In some embodiments, the diseased cells have been previously treated with a perturbation (e.g., by one or more robotic devices that automatically apply the perturbation and/or by a human that applies the genetic, chemical or physical perturbation), which may be determined in previous iteration(s) of the workflow. In some embodiments, the diseased cells have been previously treated with both a genetic perturbation and a chemical perturbation. In some embodiments, the perturbation is a chemical treatment, a therapeutic agent, a genetic modification, a change in media or any combination thereof. Time series image data may be captured at any desired interval. For instance, a burst of time-series images or video data may be captured for any duration (e.g., time series image data may be collected over a period of several milliseconds, one-tenth of a second, one second, one minute, five minutes, ten minutes, thirty minutes) once per hour, once per day, once per week, and so on.

In some embodiments, the system performs label-free time-series imaging. In other words, the system performs imaging of the live biological cells without relying on fluorescence dyes to label different cellular components. In some embodiments, the system performs quantitative phase imaging ("QPI") to obtain a time series of phase images depicting the positional and morphological characteristics in particular cellular substructures. Because different components in cells shift differently based on the phase of light traveling through them, capturing these shifts through time-series QPI allows sub-micron resolution observations. QPI produces a time series of images with enhanced information compared to ordinary light contrast microscopy and, due to inherent coherence gate effects, enables observation of live cells' activity even in scattering milieu such as a 3D collagen matrix. Further, QPI enables the observation of cells with minimum photo-toxicity. Thus, QPI can be used to speed up in vitro assay development and can provide unique insights on the dynamics of live biological processes.

In some embodiments, the system uses low photo-toxicity fluorescence and autofluorescence multi spectral imaging techniques to obtain a time series of fluorescence images and/or time series of autofluorescence images of the live biological cells. In some embodiments, the time-series image data of live biological cells (e.g., time series of phase images, time series of fluorescence images, and/or time series of autofluorescence images, etc.) are captured using a microscope according to an optical setup. The optical setup can include an illumination pattern for illuminating the live biological cells. In some embodiments, the illumination pattern can be determined dynamically during the process 104.

At block 106, the system performs machine-learning-based image processing on the time-series image data 104 of the live biological cells to obtain cell representations 108. In some embodiments, the system deploys self-supervised learning (SSL) techniques in which the machine-learning model(s) learn from unlabeled sample data, as described in detail herein. For example, the system can input a set of time-series image data comprising a time series of images of live biological cells into one or more trained self-supervised learning models, which are configured to receive a set of time-series of data and output a summary embedding (i.e., a vectors) representing the set of time-series of image data in a latent space. The summary embedding can be a vector representation of the input set of time-series of image data in the latent space. Translating an input set of time-series image data into a summary embedding can significantly reduce the size and dimension of the original data. The lower-dimension summary embeddings can be used for downstream processing, as described herein.

In some embodiments, at block 106, the system determines the summary embedding based on a sequence of embeddings by inputting the set of time-series image data into a first trained machine learning model to determine the sequence of embeddings and then determines a summary embedding based on the sequence of embeddings by inputting the sequence of embeddings into a second trained machine learning model. In some embodiments, the sequence of embeddings includes a sequence of embeddings for a single cell depicted in the set of time-series image data, and the embeddings may represent morphological or positional characteristics of the cell or cellular substructures and/or processes independent of the time the respective image of the cell in the time-series image data was acquired. In other words, each embedding can represent morphological or positional characteristics of the cell or cellular substructures and/or processes at a particular time point (e.g., a single frame in the set of time-series image data), such that the sequence represents the plurality of morphological or positional characteristics of the cell or cellular substructures and/or processes at a plurality of respective time points. In some embodiments, the summary embedding can account for dynamics (e.g., subcellular movements) between subsequent frames in the set of time-series image data. As such, the summary embedding accounts for a time axis in the set of time-series image data.

In some embodiments, the machine learning model trained to determine a sequence of embeddings is a trained self-supervised machine learning model. In some embodiments, the machine learning model is trained using an unlabeled training dataset, and the unlabeled training dataset may include a plurality of images of biological samples. For example, the self-supervised learning model can be a DINO Vision Transformer, a SimCLR model, or any other model that learns from unlabeled sample data. In some embodiments the machine learning model is pre-trained using unlabeled images that do not depict biological samples and retrained using unlabeled images of biological samples. In some embodiments, the machine learning model used to determine a sequence of embeddings is trained together with a machine learning model used to determine a summary embedding for each sequence of embeddings and a machine learning model used to determine a value (e.g., a classification) for each summary embedding, for instance, as described with respect to FIGS. 3A and 3B.

In some embodiments, the machine learning model trained to determine summary embeddings is a trained self-supervised machine learning model. In some embodiments, the model trained to determine summary embeddings can be a transformer model, a recurrent neural network ("RNN"), a long short-term network ("LSTM"), or any combination thereof. In some embodiments, a summary embedding is instead determined directly from the set of time series image data by inputting the set of time-series image data into a trained machine learning model that can process a set of imaging sequences directly (e.g., a model that can directly process video data). In such embodiments, the machine learning model may include a Video Transformer Network or a three-dimensional convolutional neural network, as shown below in FIG. 3B.

Before the machine learning models described above are used to process input time-series image data (e.g., time series image data 104), each needs to be trained. In some embodiments, training a machine learning model for determining a sequence of embeddings, a machine learning model for determining a summary embedding, and a machine learning model for determining a value based on the summary embedding (e.g., classifying the summary embedding) includes training each of the models together, for instance as described with respect to FIG. 3A. In some embodiments, a trained machine learning model for determining a summary embedding directly based on input time-series image data is trained together with a machine learning model for determining a value based on the summary embedding (e.g., classifying the summary embedding), for instance, as described with respect to FIG. 3B.

Figure 4:
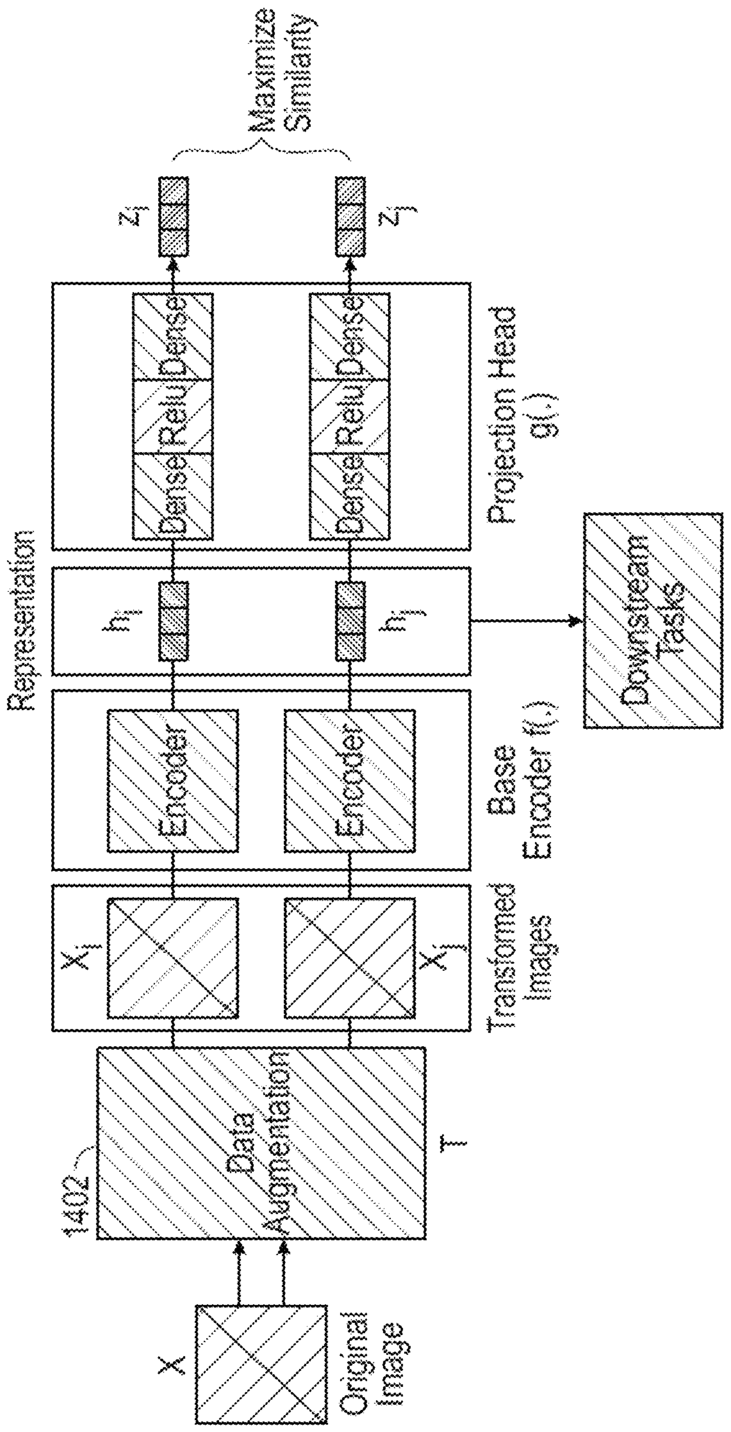
FIG. 4 illustrates training of an exemplary contrastive learning algorithm, in accordance with some embodiments.

In some embodiments, one or more of the trained machine learning models are self-supervised machine learning models that are pre-trained using unlabeled images that do not depict biological samples. In some embodiments, the models are retrained or fine-tuned using unlabeled images of biological samples, such as phase images. In some embodiments, the models are continuously updated on all imaging experiments to gather information about all existing cell types, perturbations and imaging conditions. FIG. 4, discussed below, illustrates training of an exemplary contrastive learning algorithm for determining embeddings based on input image data, in accordance with some embodiments.

In some embodiments, one or more of the self-supervised models can be trained using non-microscopy images and then used to process live cell time-series image data in block 106 in FIG. 1. In some embodiments, the model is first trained using non-microscopy images, then fine-tuned (e.g., retrained) using live cell images for a number of epochs, and then used to process input time-series image data from live cells in block 106 in FIG. 1. In some embodiments, the live cell images used to fine-tune the model can be selected from the images 104 in FIG. 1. In other words, the live cell images may be first used to train the model, and then inputted into the trained model to obtain embeddings and summary embeddings.

In some embodiments, at block 106, the system performs segmentation on the live cell time-series image data, (e.g., cell detection, nucleus detection). In some embodiments, the system performs quality control on the live cell time-series image data to obtain quality control measures, which can be used to remove artifacts, determine which live cell time-series image data are used for downstream processing in 110, etc.

At block 110, the system performs data analysis. In some embodiments, the system can determine the cell state of the one or more cells of the subject by inputting a summary embedding into a trained machine learning model. In some embodiments, the trained machine learning model includes a trained classifier. In some embodiments, the trained machine-learning model includes a linear regression classifier configured to receive a summary embedding and output a classification of a cell state (e.g., healthy or diseased). In some embodiments, the machine-learning model includes a regression classifier, such as a linear regression classifier or a logistic regression classifier, configured to receive a summary embedding and output a degree of a disease state.

In some embodiments, the cell state is indicative of a diseased state (i.e., mutant state), a healthy state (i.e., wildtype state), or a degree of the diseased state. The cell state may be indicative of a level of metabolic activity or a kinetic state. In some embodiments, the cell state is indicative of an accumulation of lipids.

In some embodiments, the system is configured to determine one or more relationships between the determined cell state, and, for instance, morphological or positional characteristics of the cell or cellular substructures depicted in the time-series image data. For example, the system may determine based on the cell state of the one or more cells and the set of time-series image data, a relationship between one or more time-variant morphological characteristics depicted in the set of time-series image data and the cell state of the one or more cells. In some embodiments, the system may determine based on the cell state of the one or more cells and the set of time-series image data, a relationship between one or more subcellular or cellular movements or processes depicted in the set of time-series image data and the cell state of the one or more cells.

In some embodiments, a user of the system can, based on the determined cell state, review the set of time series image data to, for instance, interpret the processes and/or morphological or positional characteristics of the cell and/or cellular substructures resulting in the determined cell state. For instance, a relationship may be identified between a determined cell state and any one or more of proteins/cargo transport along neurites, changes to neurite network geometries, and movement of large lipid aggregates within cells (specifically the rate of diffusion and mass transport), which may serve as a proxy for metabolic activity. In some embodiments, an exemplary system may be configured to map a network of one or both of axons and neurites to a cell of the one or more cells based on the set of time-series image data and the cell state of the one or more cells.

In some embodiments, the system is configured to determine a rate of change in the cell state. In some embodiments, a rate of change in the cell state is indicative of a variation of a cellular process, wherein the cellular process includes any one or more of a cargo transport, an organelle assembly, and an organelle disassembly. In other words, changes in cell state, or the rate of change in a cell state can serve as a proxy for underlying cellular variations.

In some embodiments, the summary embeddings can be used to determine the impact of a perturbation (e.g., a chemical treatment, a therapeutic agent, a genetic modification, a change in media, or any combination thereof) in slowing down or reversing the progression of a disease by detecting shifts in cell morphology classification. In some embodiments, the summary embeddings can be used to generate a disease model (e.g., evaluation of toxicity). In some embodiments, the summary embeddings can be used to study a characteristic of interest of a cell culture, such as proliferation rate, cell health, cell development, etc., which can be then used to optimize the culture conditions, either in real time for the cell culture under study from which the embeddings were generated or in subsequent cell cultures. In some embodiments, the summary embeddings can be used to identify conditions for progressing cells towards a desired cell state and identify combinatorial treatment and drug synergy in chemical and genetic screens.

Figure 2:
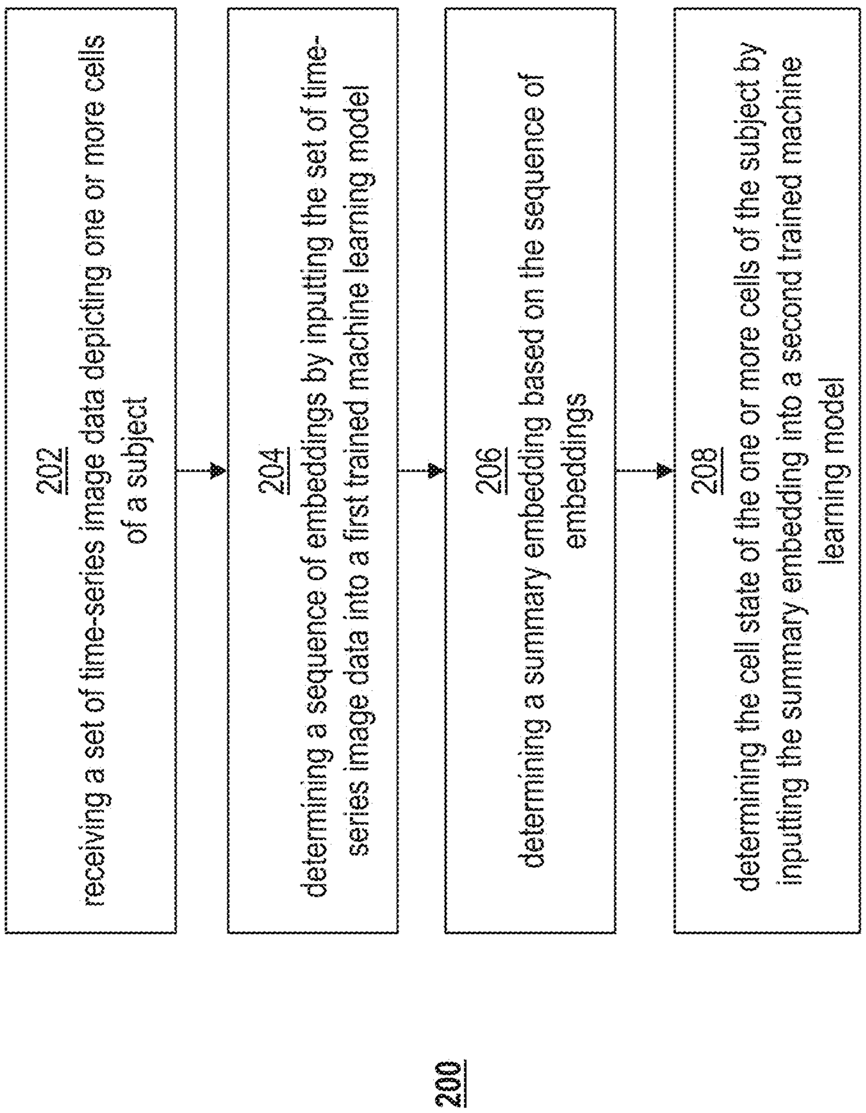
FIG. 2 illustrates an exemplary method for determining a cell state, in accordance with some embodiments.

FIG. 2 illustrates an exemplary process for determining a cell state of one or more cells of a subject, in accordance with some embodiments. Process 200 is performed, for example, using one or more electronic devices implementing a software platform. In some examples, process 200 is performed using one or more electronic devices. In some embodiments, process 200 is performed using a client-server system, and the blocks of process 200 are divided up in any manner between the server and one or more client devices. Thus, while portions of process 200 are described herein as being performed by particular devices, it will be appreciated that process 200 is not so limited. In process 200, some blocks are, optionally, combined, the order of some blocks is, optionally, changed, and some blocks are, optionally, omitted. In some examples, additional steps may be performed in combination with the process 200. Accordingly, the operations as illustrated (and described in greater detail below) are exemplary by nature and, as such, should not be viewed as limiting.

At block 202, an exemplary system (e.g., one or more electronic devices) receives a set of time-series image data depicting one or more cells of a subject. In some embodiments, the set of time-series image data includes a time series of images. In some embodiments, the set of time-series image data includes a video segment. In some embodiments, the set of time series image data includes image data acquired at a frame rate of at least four frames per second, at least eight frames per second, or the like.

In some embodiments, the set of time-series image data includes a plurality of phase images, and the plurality of phase images can be captured using an imager with a frame rate of greater than at least 4 frames per second. In some embodiments, the plurality of phase images are captured using an imager with a frame rate of about 40 frames per second. In some embodiments, the set of time-series image data includes a plurality of phase images, and the plurality of phase images can be captured using an imager with a frame rate of greater than at least 1 frame per second. In some embodiments, the plurality of phase images are captured using an imager with a frame rate of about 8 frames per second. For example, the plurality of phase images may be captured using a high-speed phase imaging device, such as a Phasics SID4-sC8 camera attachment or the Nanolive 3D Cell Explorer 96 focus, which enable the recovery of quantitative phase delay (in radians). In some embodiments, the exemplary system receives two or more burst images at a single position using the high-speed phase imaging device. In some embodiments, the phase images provide an unbiased measurement by imaging the refractive index of the cell as a whole, thus providing an unbiased measurement (e.g., as compared to the imaging and tracking of a label within a cell, as described below with regard to fluorescence imaging).

In some embodiments, the set of time-series image data includes a plurality of fluorescence images, which may be captured using an imager with a frame rate of at least 4 frames per second. In some embodiments, the plurality of fluorescence images, may be captured using an imager with a frame rate of about 100 frames per second. In some embodiments, the set of time-series image data includes a plurality of fluorescence images, which may be captured using an imager with a frame rate of at least 1 frame per second. In some embodiments, the plurality of fluorescence images, may be captured using an imager with a frame rate of about 8 frames per second. Fluorescence imaging enables an immunochemistry readout by applying labels to cells that attach to various substances in a cell that would aggregate a lipid droplet or other substances that aggregate in certain areas of the cell. As such, the labels enable tracking movement of the targeted substance within the cell. For instance, the plurality of fluorescence images may be captured using a Scientific Complementary Metal Oxide Semiconductor (sCMOS) camera, such as a Hamamatsu ORCA-Fusion Digital Scientific CMOS camera or an Andor Zyla 5.5. Acquisition of the set of time-series image data may be enabled using open-source microscopy software with a custom python layer used to implement specific hardware control.

In some embodiments, the set of time-series image data includes a plurality of phase images captured prior to a plurality of fluorescence images. This acquisition configuration can enable the cross-registration and validation of both phase and immunohistochemistry readouts at the same location (e.g., region of interest of a cell), which may be used as labels to confirm the biological origin of a change in refractive index. In addition, fluorescence channel may be useful as a phenotypic readout in many cases. Both fluorescence imaging and quantitative phase delay may be used as data to train a machine learning classifier.

In some embodiments, the one or more cells depicted in the set of time-series image data include one or more live biological cells. In some embodiments, the one or more live biological cells include one or more mammalian cells. In some embodiments, the one or more live biological cells include one or more neurons. In some embodiments, the one or more live biological cells can include healthy cells, diseased cells, or any combination thereof. For example, the one or more cells may include any of the cells described in the Examples section below.

In some embodiments, the one or more live biological cells include one or more genetic mutations, which may be selected from the group consisting of a deletion mutation, insertion mutation, substitution mutation, missense mutation, nonsense mutation, and frameshift mutation. The one or more live biological cells including one or more genetic mutations can have a phenotypic difference compared to healthy cells that do not include the one or more genetic mutations. The phenotypic difference can include a difference in metabolic activity, cellular kinetics, cellular morphology, or any combination thereof.

In some embodiments, the set of time-series image data depicts a single cell. In some embodiments, the single cell is identified using an image segmentation model. In some embodiments, the set of time-series image data is preprocessed upon receipt according to one or more preprocessing steps, for instance, to identify single cells in the set of time-series image data and center image tiles on the individual cells. In some embodiments, the set of time-series image data depicts a single cell and one or more subcellular structures and/or processes. For example, the set of time-series image data may depict a single cell and one or more neurites. The set of time-series image data may depict a single cell and one or more axons and/or dendrites. As such, the set of time-series image data may depict a single cell and one or more regions of interest associated with the cell.

At block 204, the system can determine a sequence of embeddings by inputting the set of time-series image data into a trained machine learning model. In some embodiments, the sequence of embeddings includes a sequence of embeddings for a single cell depicted in the set of time-series image data, and the embeddings may represent morphological or positional characteristics of the cell or cellular substructures and/or processes independent of the time the respective image of the cell in the time-series image data was acquired. In other words, each embedding can represent morphological or positional characteristics of the cell or cellular substructures and/or processes at a particular time point (e.g., a single frame in the set of time-series image data), such that the sequence represents the plurality of morphological or positional characteristics of the cell or cellular substructures and/or processes at a plurality of respective time points.

In some embodiments, the trained machine learning model at block 204 includes a self-supervised machine learning model. In some embodiments, the machine learning model is trained using an unlabeled training dataset, and the unlabeled training dataset may include a plurality of images of biological samples. For example, the self-supervised learning model can be a DINO Vision Transformer, a SimCLR model, or any other model that learns from unlabeled sample data. In some embodiments the machine learning model is pre-trained using unlabeled images that do not depict biological samples and retrained using unlabeled images of biological samples.

At block 206, the system can determine a summary embedding based on the sequence of embeddings. In some embodiments, the summary embedding includes a temporal dimension based on temporal information associated with the sequence of embeddings. In some embodiments, the temporal information associated with the sequence of embeddings comprises a temporal relationship between a first embedding in the sequence of embeddings and a second embedding in the sequence of embeddings. In some embodiments, the temporal information associated with the sequence of embeddings comprises a sequential relationship between a first embedding in the sequence of embeddings and a second embedding in the sequence of embeddings. In some embodiments, the temporal information of a group of embeddings is compared with another group of embeddings from the measurement sequence. These groups may be compared using Fourier or Wavelet analyses, for example, and may be used to analyze trends occurring at different temporal frequencies. In some embodiments, the temporal information associated with the sequence of embeddings comprises a time stamp associated with each embedding in the sequence of embeddings.

The summary embedding can account for dynamics (e.g., subcellular movements) between subsequent frames in the set of time-series image data. As such, the summary embedding accounts for a time axis in the set of time-series image data. In some embodiments, the summary embedding determined based on the sequence of embeddings can be determined by inputting the sequence of embeddings into a trained machine learning model. The trained machine learning model at block 206 can include a transformer model, a recurrent neural network ("RNN"), a long short-term network ("LSTM"), or any combination thereof.

In some embodiments, a summary embedding is instead determined directly from the set of time series image data by inputting the set of time-series image data into a trained machine learning model that can process a set of imaging sequences directly (e.g., a model that can directly process video data). In such embodiments, the machine learning model may include a Video Transformer Network or a three-dimensional convolutional neural network, as shown below in FIG. 3B.

At block 208, the system can determine the cell state of the one or more cells of the subject by inputting the summary embedding into a trained machine learning model. In some embodiments, the trained machine learning model at block 208 includes a trained classifier. In some embodiments, the trained machine-learning model at block 208 includes a linear regression classifier configured to receive a summary embedding and output a classification of a cell state (e.g., healthy or diseased). In some embodiments, the machine-learning model at block 208 includes a regression classifier, such as a linear regression classifier or a logistic regression classifier, configured to receive a summary embedding and output a degree of a disease state.

In some embodiments, the cell state is indicative of a diseased state (i.e., mutant state), a healthy state (i.e., wildtype state), or a degree of the diseased state. The cell state may be indicative of a level of metabolic activity or a kinetic state. In some embodiments, the cell state is indicative of an accumulation of lipids.

In some embodiments, the system is configured to determine one or more relationships between the determined cell state, and, for instance, morphological or positional characteristics of the cell or cellular substructures depicted in the time-series image data. For example, the system may determine based on the cell state of the one or more cells and the set of time-series image data, a relationship between one or more time-variant morphological characteristics depicted in the set of time-series image data and the cell state of the one or more cells. In some embodiments, the system may determine based on the cell state of the one or more cells and the set of time-series image data, a relationship between one or more subcellular or cellular movements or processes depicted in the set of time-series image data and the cell state of the one or more cells.

In some embodiments, a user of the system can, based on the determined cell state, review the set of time series image data to, for instance, interpret the processes and/or morphological or positional characteristics of the cell and/or cellular substructures resulting in the determined cell state. For instance, a relationship may be identified between a determined cell state and any one or more of proteins/cargo transport along neurites, changes to neurite network geometries, and movement of large lipid aggregates within cells (specifically the rate of diffusion and mass transport), which may serve as a proxy for metabolic activity. In some embodiments, an exemplary system may be configured to map a network of one or both of axons and neurites to a cell of the one or more cells based on the set of time-series image data and the cell state of the one or more cells.

In some embodiments, the system may be configured to determine a rate of change in the cell state. In some embodiments, a rate of change in the cell state is indicative of a variation of a cellular process, wherein the cellular process includes any one or more of a cargo transport, an organelle assembly, and an organelle disassembly. In other words, changes in cell state, or the rate of change in a cell state can serve as a proxy for underlying cellular variations.

Figure 3A:
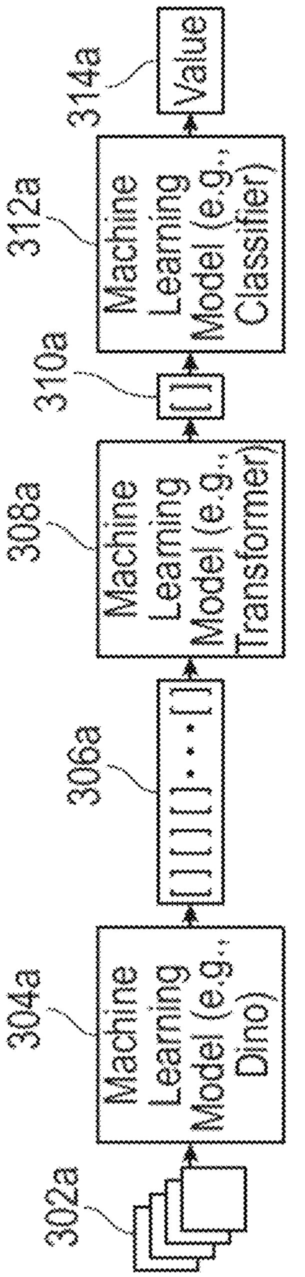
FIG. 3A illustrates an exemplary first machine learning model for determining a sequence of embeddings, an exemplary second machine learning model for determining summary embeddings, and a third trained machine learning model for classifying the summary embeddings, in accordance with some embodiments.
Figure 3B:
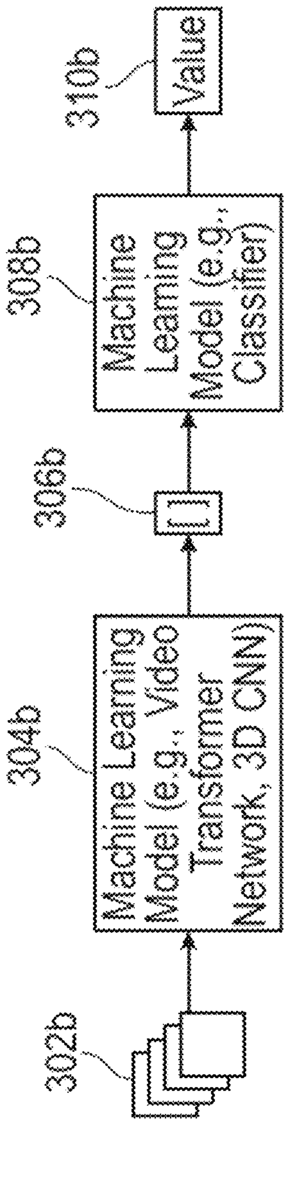
FIG. 3B illustrates an exemplary machine learning model for determining a summary embedding based on a set of time-series image data, in accordance with some embodiments.

As described above, in some embodiments, a sequence of embeddings can be determined by inputting the set of time-series image data into a first trained machine learning model, and a summary embedding can be determined based on the sequence of embeddings by inputting the sequence of embeddings into a second machine learning model. In other embodiments, a summary embedding may be determined directly by inputting the set of time series image data into a trained machine learning model configured to directly process time-series image data to generate summary embeddings. FIGS. 3A and 3B illustrate each of the aforementioned configurations.

FIG. 3A illustrates an exemplary first trained machine learning model for determining a sequence of embeddings, an exemplary second trained machine learning model for determining a summary embedding, and a third trained machine learning model for classifying the summary embeddings determined by the second trained machine learning model, in accordance with some embodiments.

In some embodiments, an exemplary system (e.g., one or more electronic devices) receives a set of time-series image data 302*a* depicting one or more cells. In some embodiments, the set of time-series image data includes a time series of images. In some embodiments, the set of time-series image data includes a video segment. In some embodiments, the set of time series image data includes image data acquired at a frame rate of at least four frames per second. In some embodiments, the set of time series image data includes image data acquired at a frame rate of at least eight frames per second. The set of time-series image data can include a plurality of phase images, and the plurality of phase images can be captured using an imager with a frame rate at least 4 frames per second. In some embodiments, the plurality of phase images are captured using an imager with a frame rate of about 40 frames per second. In some embodiments, the set of time-series image data includes a plurality of phase images, and the plurality of phase images can be captured using an imager with a frame rate of greater than at least 1 frame per second. In some embodiments, the plurality of phase images are captured using an imager with a frame rate of about 8 frames per second. For example, the plurality of phase images may be captured using a high-speed phase imaging device, such as a Phasics SID4-sC8 camera attachment or the Nanolive 3D Cell Explorer 96 focus, which enables the recovery of quantitative phase delay (in radians). In some examples, the exemplary system receives two or more burst images at a single position using the high-speed phase imaging device.

The set of time-series image data may include a plurality of fluorescence images, which are captured using an imager with a frame rate of at least 4 frames per second. In some embodiments the plurality of fluorescence images are captured using an imager with a frame rate of about 100 frames per second. In some embodiments, the set of time-series image data includes a plurality of fluorescence images, which may be captured using an imager with a frame rate of at least 1 frame per second. In some embodiments, the plurality of fluorescence images, may be captured using an imager with a frame rate of about 8 frames per second. The plurality of fluorescence images are captured using a Scientific Complementary Metal Oxide Semiconductor (sCMOS) camera, such as a Hamamatsu ORCA-Fusion Digital Scientific CMOS camera or an Andor Zyla 5.5. Acquisition of the set of time-series image data may be enabled using open-source microscopy software with a custom python layer used to implement specific hardware control.

In some embodiments, the set of time-series image data includes a plurality of phase images captured prior to a plurality of fluorescence images. As described above with reference to FIG. 2, this acquisition configuration can enable the cross-registration of both phase and immunohistochemistry readouts at the same location (e.g., a region of interest of a cell), which may be used as labels to confirm the biological origin of a change in refractive index. In addition, fluorescence channel may be useful as a phenotypic readout in many cases. Both fluorescence imaging and quantitative phase delay may be used as data to train a machine learning classifier.

In some embodiments, the one or more cells depicted in the set of time-series image data include or more live biological cells. The one or more live biological cells can include one or more mammalian cells. The one or more live biological cells can include one or more neurons. The one or more live biological cells can include healthy cells, diseased cells, or any combination thereof.

In some embodiments, the one or more live biological cells include one or more genetic mutations, which may be selected from the group consisting of a deletion mutation, insertion mutation, substitution mutation, missense mutation, nonsense mutation, and frameshift mutation. The one or more live biological cells that include one or more genetic mutations can have a phenotypic difference compared to healthy cells that do not include the one or more genetic mutations. The phenotypic difference can include a difference in metabolic activity, cellular kinetics, cellular morphology, or any combination thereof.

In some embodiments, the set of time-series image data is preprocessed upon receipt according to one or more preprocessing steps, for instance, to identify single cells in the set of time-series image data and center image tiles on the individual cells. As such, in some embodiments, the set of time-series image data depicts a single cell. The single cell may be identified using an image segmentation model. In some embodiments, the set of time-series image data depicts a single cell and one or more subcellular structures and/or processes. For example, the set of time-series image data may depict a single cell and one or more neurites. The set of time-series image data may depict a single cell and one or more axons and/or dendrites. As such, the set of time-series image data may depict a single cell and one or more regions of interest associated with the cell.

In some embodiments, the system can determine a sequence of embeddings 306*a* by inputting the set of time-series image data into a first trained machine learning model 304*a*. In some embodiments, the sequence of embeddings 306*a* includes a sequence of embeddings for a single cell depicted in the set of time-series image data, and the embeddings may represent morphological or positional characteristics of the cell or cellular substructures and/or processes independent of the time the respective image of the cell in the time-series image data was acquired. In other words, each embedding can represent morphological or positional characteristics of the cell or cellular substructures and/or processes at a particular time point (e.g., a single frame in the set of time-series image data), such that the sequence represents the plurality of morphological or positional characteristics of the cell or cellular substructures and/or processes at a plurality of respective time points.

In some embodiments, the first trained machine learning model 304*a* includes a self-supervised machine learning model. The first trained machine learning model can be trained using an unlabeled training dataset, and the unlabeled training dataset may include a plurality of images of biological samples. In some embodiments, the self-supervised learning model is a DINO Vision Transformer, a SimCLR model, or any other model that learns from unlabeled sample data. In some embodiments the first trained machine learning model is pre-trained using unlabeled images that do not depict biological samples and retrained using unlabeled images of biological samples.

The system can determine a summary embedding 310*a* based on the sequence of embeddings 306*a*. In some embodiments, the summary embedding includes a temporal dimension based on temporal information associated with the sequence of embeddings. In some embodiments, the temporal information associated with the sequence of embeddings comprises a temporal relationship between a first embedding in the sequence of embeddings and a second embedding in the sequence of embeddings. In some embodiments, the temporal information associated with the sequence of embeddings comprises a sequential relationship between a first embedding in the sequence of embeddings and a second embedding in the sequence of embeddings. In some embodiments, the temporal information associated with the sequence of embeddings comprises a time stamp associated with each embedding in the sequence of embeddings.

The summary embedding accounts for dynamics (e.g., subcellular movements) occurring between subsequent frames in the set of time-series image data. As such, the summary embedding accounts for a time axis in the set of time-series image data. In some embodiments, the system determines the summary embedding 310*a* by inputting the sequence of embeddings 306*a* into a second trained machine learning model 308*a*. The second trained machine learning model 308*a* can include a transformer model, a recurrent neural network ("RNN"), a long short-term network ("LSTM"), or any combination thereof.

In some embodiments, the system can determine a value 314*a* (e.g., a cell state) by inputting the summary embedding 310*a* into a third trained machine learning model 312*a*. In some embodiments, the trained machine-learning model 312*a* includes a linear regression classifier configured to receive a summary embedding and output a classification of a cell state (e.g., healthy or diseased). In some embodiments, the third trained machine learning model includes a regression classifier, such as a linear regression classifier or a logistic regression classifier, configured to receive a summary embedding and output a degree of a disease state.

In some embodiments, training machine learning model 304*a*, machine learning model 308*a*, and machine learning model 312*a* includes training each of the models together by inputting time series image data (e.g., a time series of images depicting either healthy or sick cells) into the machine learning model 304*a* to generate a sequence of embeddings, inputting the sequence of embeddings into the machine learning model 308*a* to generate a summary embedding based on the sequence of embeddings, and inputting the summary embedding into the machine learning model 312*a* to determine a value (e.g., a classification of a cell state or a degree of a disease state). The classification may then be compared to ground truth values and classification errors may be backpropagated.

FIG. 3B illustrates an exemplary machine learning model for determining a summary embedding based on a set of time-series image data, in accordance with some embodiments. In some embodiments, an exemplary system (e.g., one or more electronic devices) receives a set of time-series image data 302*b* depicting one or more cells. The set of time-series image data can include any of the time-series image data described above with reference to FIGS. 2 and 3A The system can determine a summary embedding 306*b* based on the set of time series image data by inputting the set of time series image data into a trained machine learning model 304*b*. In some embodiments, the summary embedding comprises a temporal dimension based on temporal information associated with the sequence of embeddings. In some embodiments, the temporal information associated with the sequence of embeddings comprises a temporal relationship between a first embedding in the sequence of embeddings and a second embedding in the sequence of embeddings. In some embodiments, the temporal information associated with the sequence of embeddings comprises a sequential relationship between a first embedding in the sequence of embeddings and a second embedding in the sequence of embeddings. In some embodiments, the temporal information associated with the sequence of embeddings comprises a time stamp associated with each embedding in the sequence of embeddings.

In some embodiments, the trained machine learning model 304*b* includes a Video Transformer Network model or a three-dimensional convolutional neural network trained to directly process the set of time series image data to determine a summary embedding. As described above with respect to FIGS. 2 and 3A, the summary embedding accounts for dynamics (e.g., subcellular movements) occurring between subsequent frames in the set of time-series image data. As such, the summary embedding accounts for a time axis in the set of time-series image data.

In some embodiments, the system can determine a value 310*b* (e.g., a cell state) by inputting the summary embedding 306*n* into a second trained machine learning model 308*b*. In some embodiments, the trained machine-learning model 308*b* includes a linear regression classifier configured to receive a summary embedding and output a classification of a cell state (e.g., healthy or diseased). In some embodiments, the third trained machine learning model includes a regression classifier, such as a linear regression classifier or a logistic regression classifier, configured to receive a summary embedding and output a degree of a disease state.

In some embodiments, training machine learning model 304*b* and machine learning model 308*b* includes training the models together by inputting time series image data (e.g., a time series of images depicting either healthy or sick cells) into the machine learning model 304*b* to generate a summary embedding based on the time series image data, and inputting the summary embedding into the machine learning model 308*b* to determine a value (e.g., a classification of a cell state or a degree of a disease state). The classification may then be compared to ground truth values and classification errors may be backpropagated.

FIG. 4 illustrates training of an exemplary contrastive learning algorithm, in accordance with some embodiments. One or more of the models used in FIG. 1 can be one of the encoders in FIG. 4. During training, an original image X is obtained. Data transformation or augmentation can be applied to the original image X to obtain two augmented images $X_i$ and $X_j$. For example, the system can randomly apply two separate data augmentation operators (e.g., crop, flip, color jitter, grayscale, blur) to obtain $X_i$ and $X_j$.

Each of the two augmented images $X_i$ and $X_j$ is passed through an encoder to obtain respective vector representations in a latent space. In the depicted example, the two encoders have shared weights. In some examples, each encoder is implemented as a neural network. For example, an encoder can be implemented using a variant of the residual neural network ("ResNet") architecture. As shown, the two encoders output hi (vector outputted by the encoder from $X_i$) and $h_j$ (vector outputted by the encoder from $X_j$).

The two vector representations hi and $h_j$ are passed through a projection head to obtain two projections $z_i$ and $z_j$. In some examples, the projection head comprises a series of non-linear layers (e.g., Dense-Relu-Dense layers) to apply non-linear transformation on the vector representation to obtain the projection. The projection head amplifies the invariant features and maximizes the ability of the network to identify different transformations of the same image.

During training, the similarity between the two projections $z_i$ and $z_j$ for the same image is maximized. For example, a loss is calculated based on $z_i$ and $z_j$, and the encoder is updated based on the loss to maximize a similarity between the two latent representations. In some examples, to maximize agreement (i.e., similarity) between the z-projections, the system can define the similarity metric as cosine similarity:

$$sim(u, v) = \frac{u^T v}{\|u\| \, \|v\|}$$

In some examples, the system trains the network by minimizing the normalized temperature-scaled cross-entropy loss:

$$\ell_{i,j} = -\log \frac{\exp(sim(z_i, z_j)/\tau)}{\sum_{k=1}^{2N} \mathbb{1}_{[k \neq i]} \exp(sim(z_i, z_k)/\tau)}$$

where τ denotes an adjustable temperature parameter. Accordingly, via training, the encoder learns to output a vector representation that preserves the invariant features of the input image while minimizing image-specific characteristics (e.g., imaging angle, resolution, artifacts).

Figure 5:
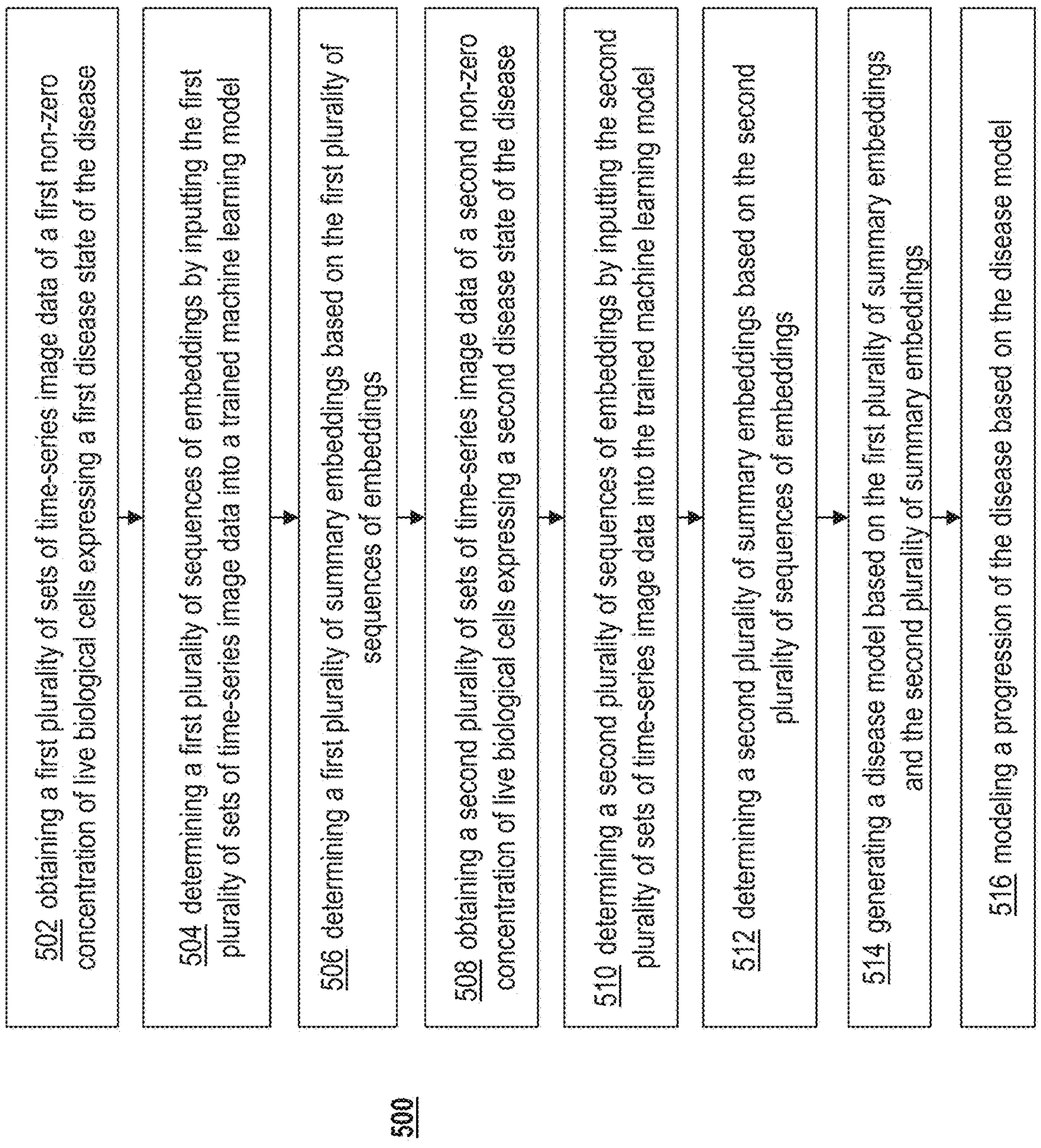
FIG. 5 illustrates an exemplary method for modeling a progression of a disease, in accordance with some embodiments.

FIG. 5 illustrates an exemplary process for modeling a progression of a disease. Process 500 is performed, for example, using one or more electronic devices implementing a software platform. In some examples, process 500 is performed using one or more electronic devices. In some embodiments, process 500 is performed using a client-server system, and the blocks of process 500 are divided up in any manner between the server and one or more client devices. Thus, while portions of process 500 are described herein as being performed by particular devices, it will be appreciated that process 500 is not so limited. In process 500, some blocks are, optionally, combined, the order of some blocks is, optionally, changed, and some blocks are, optionally, omitted. In some examples, additional steps may be performed in combination with the process 500. Accordingly, the operations as illustrated (and described in greater detail below) are exemplary by nature and, as such, should not be viewed as limiting.

At block 502, an exemplary system (e.g., one or more electronic devices) obtains a first plurality of sets of time-series image data of a first non-zero concentration of live biological cells expressing a first disease state of the disease. In some embodiments, a set of time-series image data of the first plurality of sets of time-series image data includes a time series of images. In some embodiments, a set of time-series image data of the first plurality of sets of time-series image data includes a video segment. In some embodiments, a set of time-series image data of the first plurality of sets of time-series image data includes image data acquired at a frame rate of at least four frames per second, at least eight frames per second, or the like.

In some embodiments, a set of time-series image data of the first plurality of sets of time-series image data includes a plurality of phase images. In some embodiments, the plurality of phase images is captured using an imager with a frame rate of at least 4 frames per second. In some embodiments, the frame rate of the imager used to capture the plurality of phase images is about 40 frames per second. In some embodiments, the set of time-series image data includes a plurality of phase images, and the plurality of phase images can be captured using an imager with a frame rate of greater than at least 1 frame per second. In some embodiments, the plurality of phase images are captured using an imager with a frame rate of about 8 frames per second. For example, the plurality of phase images may be captured using a high-speed phase imaging device, such as a Phasics SID4-sC8 camera attachment or the Nanolive 3D Cell Explorer 96 focus, which enables the recovery of quantitative phase delay (in radians). In some examples, the exemplary system receives two or more burst images at a single position using the high-speed phase imaging device.

In some embodiments, a set of time-series image data of the first plurality of sets of time-series image data includes a plurality of fluorescence images. In some embodiments, the plurality of fluorescence images is captured using an imager with a frame rate of at least 4 frames per second. In some embodiments, the plurality of fluorescence images is captured using an imager with a frame rate of about 100 frames per second. In some embodiments, the set of time-series image data includes a plurality of fluorescence images, which may be captured using an imager with a frame rate of at least 1 frame per second. In some embodiments, the plurality of fluorescence images, may be captured using an imager with a frame rate of about 8 frames per second. For example, the plurality of fluorescence images may be captured using a Scientific Complementary Metal Oxide Semiconductor (sCMOS) camera, such as a Hamamatsu ORCA-Fusion Digital Scientific CMOS camera or an Andor Zyla 5.5. Acquisition of the set of time-series image data may be enabled using open-source microscopy software with a custom python layer used to implement specific hardware control.

In some embodiments, a set of time-series image data of the first plurality of sets of time-series image data includes a plurality of phase images captured prior to or after a plurality of fluorescence images. This acquisition configuration can enable the cross-registration of both phase and immunohistochemistry readouts at the same location (e.g., a region of interest of a cell), which may be used as labels to confirm the biological origin of a change in refractive index. In addition, fluorescence channel may be useful as a phenotypic readout in many cases. Time-series image data acquired using both fluorescence imaging and phase imaging may be used as data to train a machine learning classifier.

In some embodiments, a set of time-series image data of the first plurality of sets of time-series image data is preprocessed upon receipt according to one or more preprocessing steps, for instance, to identify one or more single cells in the set of time-series image data and center image tiles on the individual cells. In some embodiments, a set of time-series image data of the first plurality of sets of time-series image data depicts a single cell. In some embodiments, the single cell is identified using an image segmentation model. In some embodiments, a set of time-series image data of the first plurality of sets of time-series image data depicts a single cell and one or more subcellular structures and/or processes. For example, a set of time-series image data of the first plurality of sets of time-series image data may depict a single cell and one or more neurites. A set of time-series image data of the first plurality of sets of time-series image data may depict a single cell and one or more axons and/or dendrites. As such, a set of time-series image data of the first plurality of sets of time-series image data may depict a single cell and one or more regions of interest associated with the cell.

In some embodiments, the first non-zero concentration of live biological cells includes one or more mammalian cells. In some embodiments, the first non-zero concentration of live biological cells includes one or more neurons. For instance the live biological cells may include any of those described below with respect to the Examples section below.

At block 504, the exemplary system (e.g., one or more electronic devices) determines a first plurality of sequences of embeddings by inputting the first plurality of sets of time-series image data into a trained machine learning model. In some embodiments, the trained machine learning model includes a self-supervised machine learning model. In some embodiments, the trained machine learning model is trained using an unlabeled training dataset. In some embodiments, the self-supervised learning model is a DINO Vision Transformer, a SimCLR model, or any other model that learns from unlabeled sample data. In some embodiments, the unlabeled training dataset comprises a plurality of images of biological samples. In some embodiments, the machine learning model is pre-trained using unlabeled images that do not depict biological samples and retrained using unlabeled images of biological samples.

In some embodiments, a sequence of embeddings of the first plurality of sequences of embeddings includes a sequence of embeddings for a single cell depicted in the first plurality of sets of time-series image data, and the embeddings may represent morphological or positional characteristics of the cell or cellular substructures and processes independent of the time the respective image of the cell in the time-series image data was acquired. In other words, each embedding can represent morphological or positional characteristics of the cell or cellular substructures and processes at a particular time point (e.g., a single frame in the set of time-series image data), such that the sequence represents a plurality of morphological or positional characteristics of the cell or cellular substructures at a plurality of respective time points.

At block 506, the exemplary system (e.g., one or more electronic devices) determines a first plurality of summary embeddings based on the first plurality of sequences of embeddings. In some embodiments, a summary embedding of the first plurality of summary embeddings comprises a temporal dimension based on temporal information associated with a first sequence of embeddings in the first plurality of sequences of embeddings. In some embodiments, the temporal information associated with the first sequence of embeddings comprises a temporal relationship between a first embedding in the first sequence of embeddings and a second embedding in the first sequence of embeddings. In some embodiments, the temporal information associated with the first sequence of embeddings comprises a sequential relationship between a first embedding in the first sequence of embeddings and a second embedding in the first sequence of embeddings. In some embodiments, the temporal information associated with the first sequence of embeddings comprises a time stamp associated with each embedding in the first sequence of embeddings.

In some embodiments, a summary embedding of the first plurality of summary embeddings accounts for dynamics (e.g., subcellular movements) occurring between subsequent frames in a set of time-series image data of the first plurality of sets of time series image data. As such, the summary embedding accounts for a time axis in the set of time-series image data. In some embodiments, the first plurality of summary embeddings are determined based on the first plurality of sequences of embeddings by inputting the first plurality of sequences of embeddings into a trained machine learning model. The trained machine learning model can include a transformer model, a recurrent neural network ("RNN"), a long short-term network ("LSTM"), or any combination thereof.

As described above, in some embodiments, summary embeddings can instead be determined directly from time series image data by inputting the time-series image data into a trained machine learning model that can process a set of imaging sequences directly (e.g., a model that can directly process video data). In such embodiments, the machine learning model may include a Video Transformer Network or a three-dimensional convolutional neural network, as shown in FIG. 3B.

At block 508, the exemplary system (e.g., one or more electronic devices) obtains a second plurality of sets of time-series image data of a second non-zero concentration of live biological cells expressing a second disease state of the disease. In some embodiments, a set of time-series image data of the second plurality of sets of time-series image data includes a time series of images. In some embodiments, a set of time-series image data of the second plurality of sets of time-series image data includes a video segment. In some embodiments, a set of time-series image data of the second plurality of sets of time-series image data includes image data acquired at a frame rate of at least four frames per second, at least eight frames per second, or the like.

In some embodiments, a set of time-series image data of the second plurality of sets of time-series image data includes a plurality of phase images. In some embodiments, the plurality of phase images is captured using an imager with a frame rate of at least 4 frames per second. In some embodiments, the frame rate of the imager used to capture the plurality of phase images is about 40 frames per second. In some embodiments, the set of time-series image data includes a plurality of phase images, and the plurality of phase images can be captured using an imager with a frame rate of greater than at least 1 frame per second. In some embodiments, the plurality of phase images are captured using an imager with a frame rate of about 8 frames per second. For example, the plurality of phase images may be captured using a high-speed phase imaging device, such as a Phasics SID4-sC8 camera attachment or the Nanolive 3D Cell Explorer 96 focus, which enables the recovery of quantitative phase delay (in radians). In some examples, the exemplary system receives two or more burst images at a single position using the high-speed phase imaging device.

In some embodiments, a set of time-series image data of the second plurality of sets of time-series image data includes a plurality of fluorescence images. In some embodiments, the plurality of fluorescence images is captured using an imager with a frame rate of at least 4 frames per second. In some embodiments, the plurality of fluorescence images is captured using an imager with a frame rate of about 100 frames per second. In some embodiments, the set of time-series image data includes a plurality of fluorescence images, which may be captured using an imager with a frame rate of at least 1 frame per second. In some embodiments, the plurality of fluorescence images, may be captured using an imager with a frame rate of about 8 frames per second. For example, the plurality of fluorescence images may be captured using a Scientific Complementary Metal Oxide Semiconductor (sCMOS) camera, such as a Hamamatsu ORCA-Fusion Digital Scientific CMOS camera or an Andor Zyla 5.5. Acquisition of the set of time-series image data may be enabled using open-source microscopy software with a custom python layer used to implement specific hardware control.

In some embodiments, a set of time-series image data of the second plurality of sets of time-series image data includes a plurality of phase images captured prior to a plurality of fluorescence images. This acquisition configuration can enable the cross-registration of both phase and immunohistochemistry readouts at the same location (e.g., a region of interest of a cell), which may be used as labels to confirm the biological origin of a change in refractive index. In addition, fluorescence channel may be useful as a phenotypic readout. Both Fluorescence imaging and quantitative phase delay may be used as data to train a machine learning classifier.

In some embodiments, a set of time-series image data of the second plurality of sets of time-series image data is preprocessed upon receipt according to one or more preprocessing steps, for instance, to identify one or more single cells in the set of time-series image data and center image tiles on the individual cells. In some embodiments, a set of time-series image data of the second plurality of sets of time-series image data depicts a single cell. In some embodiments, the single cell is identified using an image segmentation model. In some embodiments, a set of time-series image data of the second plurality of sets of time-series image data depicts a single cell and one or more subcellular structures and/or processes. For example, a set of time-series image data of the second plurality of sets of time-series image data may depict a single cell and one or more neurites. A set of time-series image data of the second plurality of sets of time-series image data may depict a single cell and one or more axons and/or dendrites. As such, a set of time-series image data of the second plurality of sets of time-series image data may depict a single cell and one or more regions of interest associated with the cell.

In some embodiments, the second non-zero concentration of live biological cells includes one or more mammalian cells. In some embodiments, the second non-zero concentration of live biological cells includes one or more neurons. In some embodiments, the second non-zero concentration of live biological cells may include any of the cells described in the Examples section below.

At block 510, the exemplary system (e.g., one or more electronic devices) determines a second plurality of sequences of embeddings by inputting the second plurality of sets of time-series image data into the trained machine learning model. In some embodiments, the trained machine learning model includes a self-supervised machine learning model. In some embodiments, the trained machine learning model is trained using an unlabeled training dataset. In some embodiments, the self-supervised learning model is a DINO Vision Transformer, a SimCLR model, or any other model that learns from unlabeled sample data. In some embodiments, the unlabeled training dataset comprises a plurality of images of biological samples. In some embodiments, the machine learning model is pre-trained using unlabeled images that do not depict biological samples and retrained using unlabeled images of biological samples.

In some embodiments, a sequence of embeddings of the second plurality of sequences of embeddings includes a sequence of embeddings for a single cell depicted in the second plurality of sets of time-series image data, and the embeddings may represent morphological or positional characteristics of the cell or cellular substructures and processes independent of the time the respective image of the cell in the time-series image data was acquired. In other words, each embedding can represent morphological or positional characteristics of the cell or cellular substructures and processes at a particular time point (e.g., a single frame in the set of time-series image data), such that the sequence represents a plurality of morphological or positional characteristics of the cell or cellular substructures at a plurality of respective time points.

At block 512, the exemplary system (e.g., one or more electronic devices) determines a second plurality of summary embeddings based on the second plurality of sequences of embeddings. In some embodiments, a summary embedding of the second plurality of summary embeddings comprises a temporal dimension based on temporal information associated with a second sequence of embeddings in the second plurality of sequences of embeddings. In some embodiments, the temporal information associated with the second sequence of embeddings comprises a temporal relationship between a first embedding in the second sequence of embeddings and a second embedding in the second sequence of embeddings. In some embodiments, the temporal information associated with the second sequence of embeddings comprises a sequential relationship between a first embedding in the second sequence of embeddings and a second embedding in the second sequence of embeddings. In some embodiments, the temporal information associated with the second sequence of embeddings comprises a time stamp associated with each embedding in the second sequence of embeddings.

In some embodiments, a summary embedding of the second plurality of summary embeddings accounts for dynamics (e.g., subcellular movements) occurring between subsequent frames in a set of time-series image data of the second plurality of sets of time series image data. As such, the summary embedding accounts for a time axis in the set of time-series image data. In some embodiments, the second plurality of summary embeddings are determined based on the first plurality of sequences of embeddings by inputting the first plurality of sequences of embeddings into a trained machine learning model. The trained machine learning model can include a transformer model, a recurrent neural network ("RNN"), a long short-term network ("LSTM"), or any combination thereof.

As described above, in some embodiments, summary embeddings can instead be determined directly from time series image data by inputting the time-series image data into a trained machine learning model that can process a set of imaging sequences directly (e.g., a model that can directly process video data). In such embodiments, the machine learning model may include a Video Transformer Network or a three-dimensional convolutional neural network, as shown in FIG. 3B.

At block 514, the exemplary system (e.g., one or more electronic devices) generates a disease model based on the first plurality of summary embeddings and the second plurality of summary embeddings. A disease model can represent various states of a disease in a topological space. As discussed below, for example, in the topological space, the disease model may comprise a cluster of summary embeddings corresponding to a first disease state (e.g., a healthy state), a cluster of summary embeddings corresponding to a second disease state (e.g., a less diseased state), a cluster of summary embeddings corresponding to a third disease state (e.g., a more diseased state), etc. In some embodiments, generating the disease model includes mapping the first plurality of summary embeddings and the second plurality of summary embeddings into a topological space. At block 516, the exemplary system (e.g., one or more electronic devices) models a progression of the disease based on the disease model.

In some embodiments, the system can further generate one or more representations of the first and second disease state based on clusters of embeddings in the topological space. The exemplary system can identify a location of a first cluster of summary embeddings based on the first plurality of summary embeddings in the topological space and generate a representation of the first disease state based on the location of the first cluster. The system can further identify a location of a second cluster of summary embeddings based on the second plurality of summary embeddings in the topological space and generate a representation of the second disease state based on the location of the second cluster.

In some embodiments, the system can further generate a disease axis based on the location of the first cluster and the location of the second cluster. In some embodiments, the disease axis represents a hyperplane separating a centroid of the first cluster of summary embeddings from a centroid of the second cluster of summary embeddings. In some embodiments, the system can further identify one or more embeddings in the topological space based on the disease axis and generate one or more synthetic images, using a generative model. In general, any known generative model comprising a discriminator and a generator can be used. In some embodiments, the generative model can be an autoregressive model, a variational autoencoder (VAE) model or a generative adversarial network (GAN) model. For example, the system can further identify one or more embeddings in the topological space based on the disease axis and generate one or more synthetic images, using a GAN model, based on the identified one or more embeddings. An embedding can be identified, for example, by picking a location in the topological space that represents a disease state of interest. In some embodiments, the system can further compare a phenotype depicted in the one or more synthetic images to one or more real images depicting a real cell to validate the phenotype depicted in the one or more synthetic images. The phenotype can include a neurite length, a cell size, a movement of one or more particles within a cell, or any combination thereof. In some embodiments, the imaging stage may generate fluorescence images and/or autofluorescence images of the live biological cells from transformed bright field images. Additional information of the image transformation models can be found in U.S. application Ser. No. 17/480,047 titled "BIOLOGICAL IMAGE TRANSFORMATION USING MACHINE-LEARNING MODELS," which issued as U.S. Pat. No. 11,423,256 on Aug. 23, 2022, and which is incorporated herein by reference in its entirety.

In some embodiments, the system can further determine an impact of a perturbation (e.g., a perturbagen, such as, a chemical treatment, a therapeutic agent, a genetic modification, a change in media, or any combination thereof) on a reversion of the one or more diseased live biological cells from a diseased state. To determine an impact of a perturbation on a reversion of the one or more diseased live biological cells from a diseased state the system can obtain a first set of time-series image data of one or more diseased live biological cells, determine a first sequence of embeddings by inputting the first set of time-series image data into the trained machine learning model, and determine a first summary embedding based on the first sequence of embeddings. The system can further apply a perturbation to the one or more diseased live biological cells, and, after applying the perturbation, the system can obtain a second set of time-series image data of the one or more diseased live biological cells, determine a second sequence of embeddings by inputting the second set of time-series image data into the trained machine learning model, determine a second summary embedding based on the second sequence of embeddings, and determine, based on the first summary embedding, the second summary embedding, and the disease model, an impact of the perturbation on a reversion of the one or more diseased live biological cells from a diseased state (e.g., whether the second summary embedding is closer to the healthy state in the disease model, the rate of the movement). Similar techniques can be used to evaluate different dosages of the same drug.

In some embodiments, determining the impact of the perturbation includes comparing a location of the first summary embedding in the topological space; a location of the second summary embedding in the topological space; the location of the first cluster; and the location of the second cluster. For instance, the first summary embedding may be located near a centroid of the first cluster prior to application of the perturbation. After applying the perturbation, the second summary embedding may be located closer to the second cluster, representing a reversion of a cell from the first disease state to the second disease state.

In some embodiments, the system can further determine a dosage for the perturbation (e.g., the chemical treatment or therapeutic agent) based on the determination of the impact of the perturbation. In some embodiments, the system can further determine one or more dose administration intervals for administering the perturbation based on the determination of the impact of the perturbation. In some embodiments, the perturbation is a chemical treatment, a therapeutic agent, a genetic treatment, a change in media, or any combination thereof.

Figure 6:
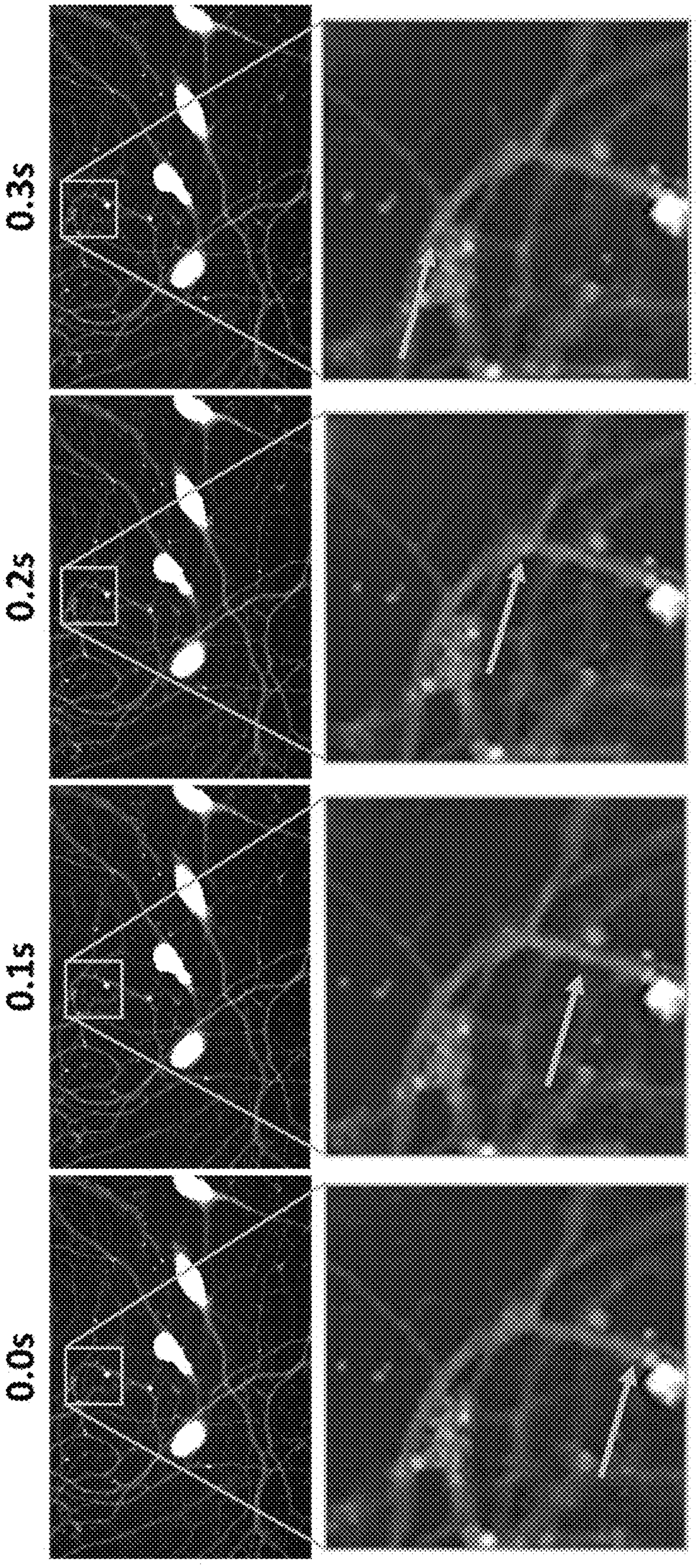
FIG. 6 illustrates exemplary time-series image data of IPSC-derived neurons imaged using QPI at 60× magnification. The inserts (bottom) illustrate particle motion along the axons, representing a dynamic process detectable with the proposed imaging method.

FIG. 6 illustrates exemplary time-series image data of IPSC-derived neurons imaged using QPI at 60× magnification. The inserts (bottom) illustrate particle motion along the axons, representing a dynamic process detectable with the proposed imaging method.

Figure 7:
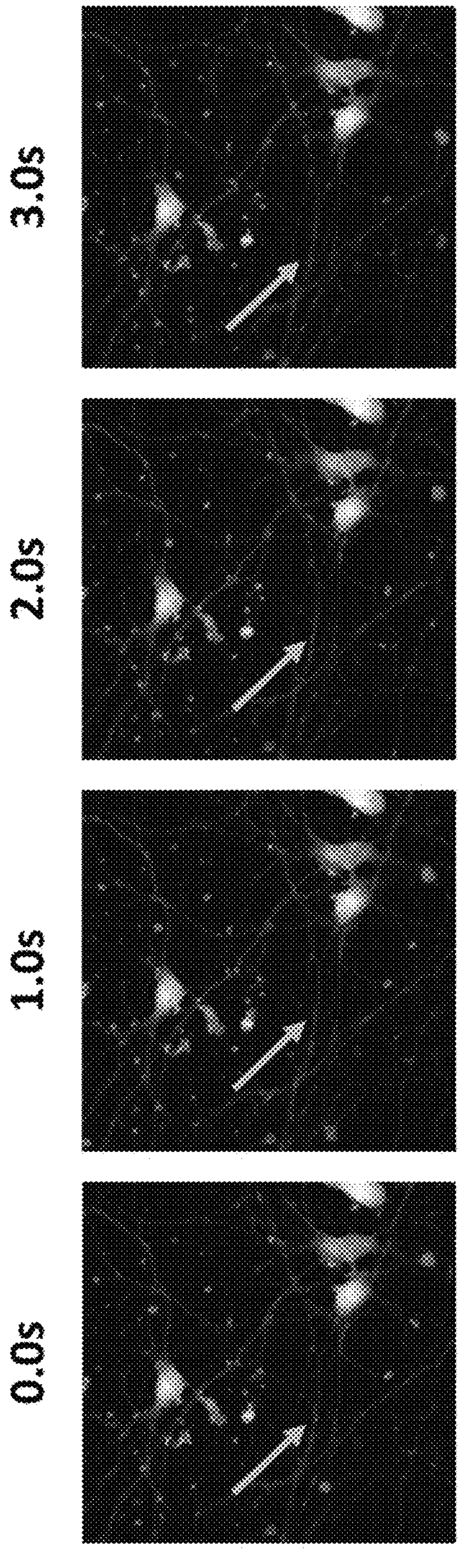
FIG. 7 illustrates exemplary time-series image data of IPSC-derived neurons imaged using QPI at 60× magnification, acquired at 10 Hz and rendered at 1 Hz. A computationally applied 3D median filter and blob detector algorithm are overlaid in red to highlight differences between time points in the QPI image.

FIG. 7 illustrates exemplary time-series image data of IPSC-derived neurons imaged using QPI at 60× magnification, acquired at 10 Hz and rendered at 1 Hz. A computationally applied 3D median filter and blob detector algorithm are overlaid in red to highlight differences between time points in the QPI image.

Figure 9:
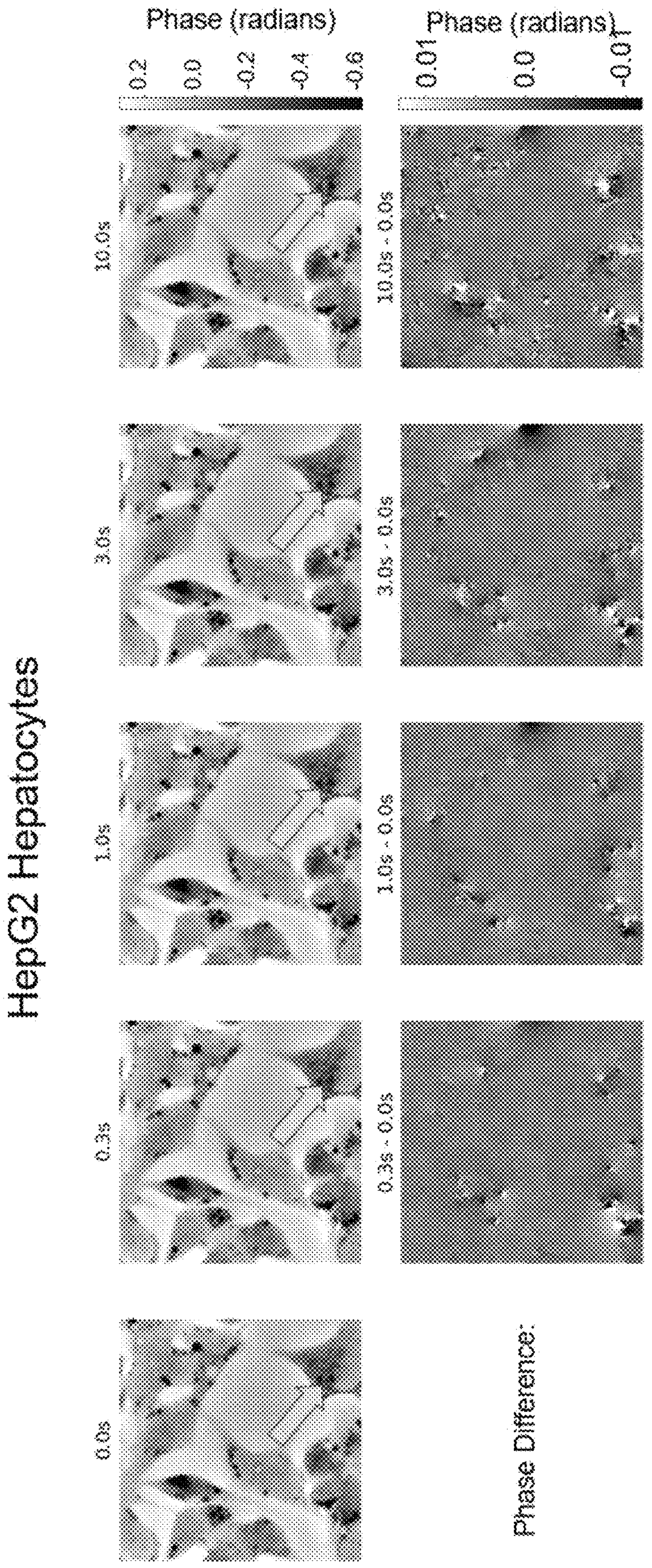
FIG. 9 illustrates exemplary intracellular dynamics, in accordance with some embodiments.

FIG. 9 illustrates exemplary intracellular dynamics, in accordance with some embodiments. Specifically, FIG. 9 depicts hepatocytes (HepG2), after a treatment, causing a known fatty droplet accumulation phenotype. The arrows indicate intracellular dynamics on 0-1 s and 1-10 s timescales.

Figure 10:
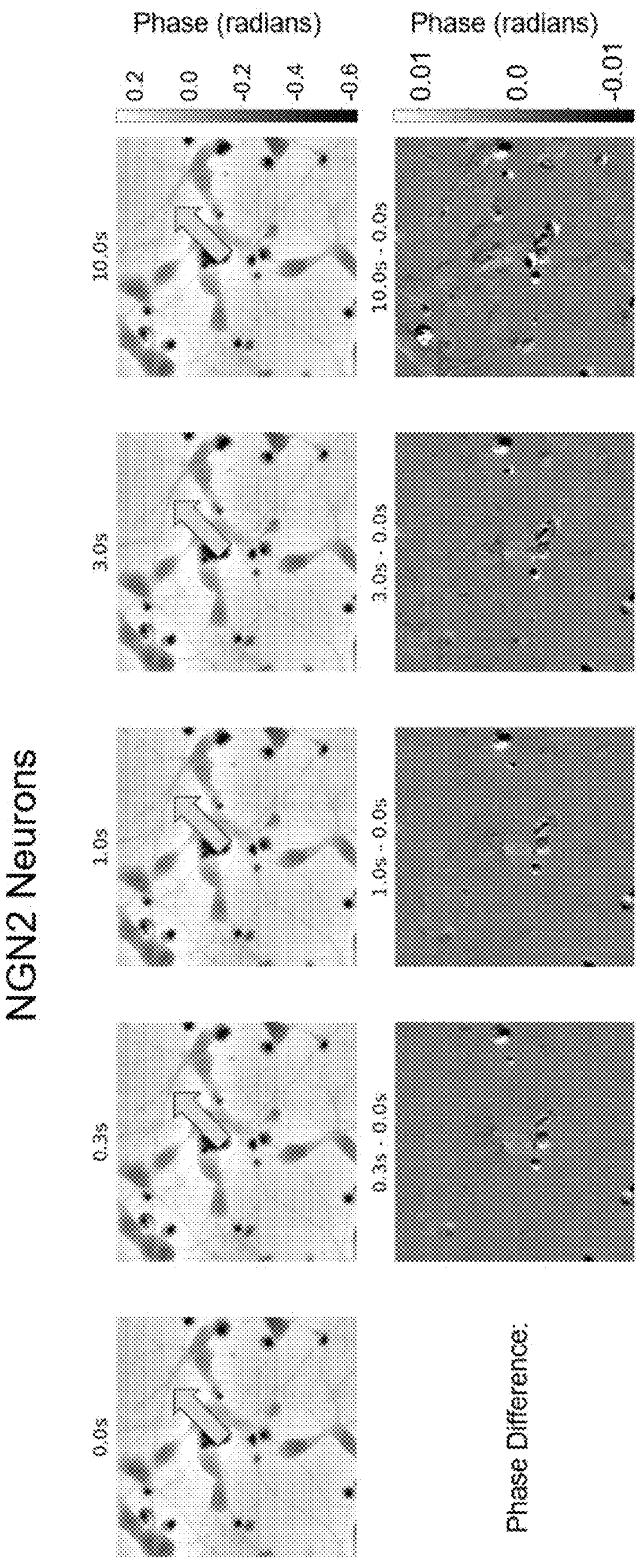
FIG. 10 illustrates exemplary intracellular dynamics, in accordance with some embodiments.

FIG. 10 illustrates exemplary intracellular dynamics, in accordance with some embodiments. Specifically, FIG. 10 depicts neurons differentiated from immunized pluripotent stem cells (iPSC), showing mass transport along the axon as well as cell movement on timescales of 0-1 s and 1-10 s.

Figure 8:
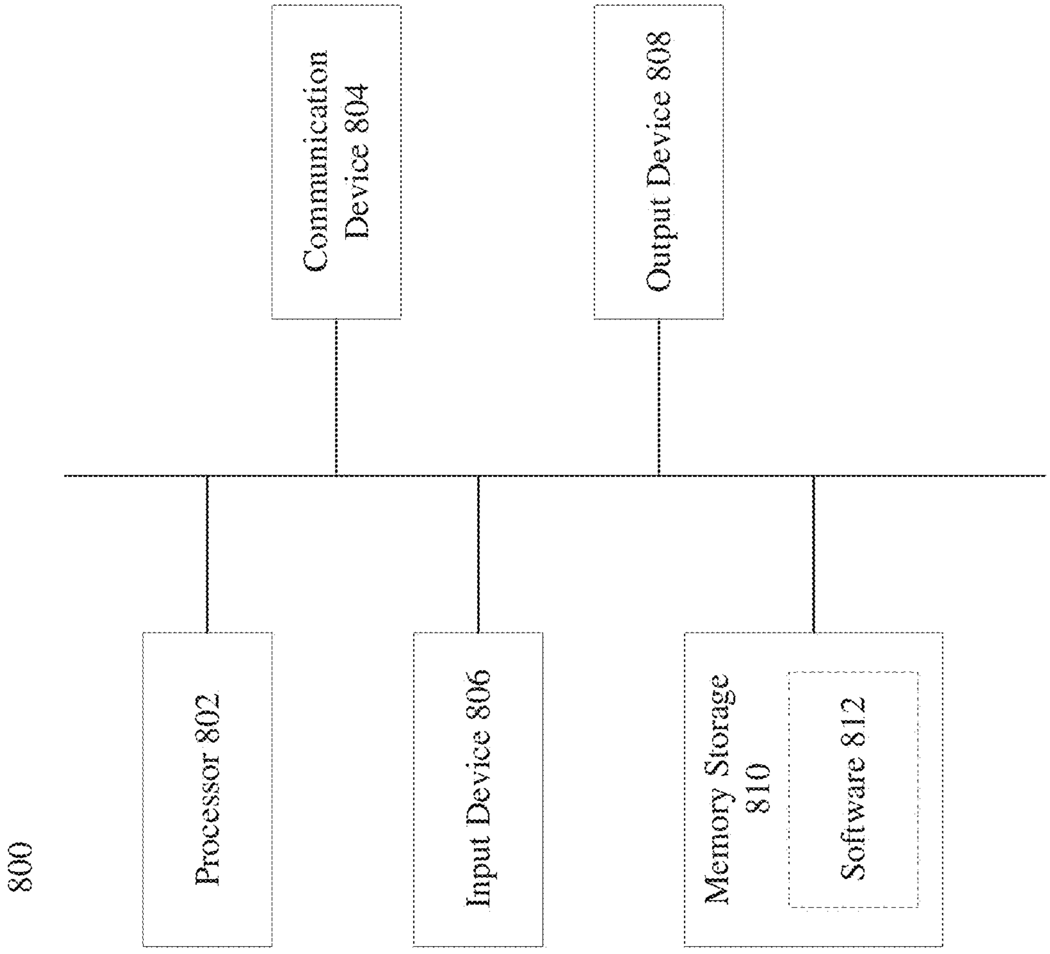
FIG. 8 illustrates an exemplary computing system, in accordance with some embodiments.

FIG. 8 depicts an exemplary computing device 800, in accordance with one or more examples of the disclosure. Device 800 can be a host computer connected to a network. Device 800 can be a client computer or a server. As shown in FIG. 8, device 800 can be any suitable type of microprocessor-based device, such as a personal computer, workstation, server, or handheld computing device (portable electronic device) such as a phone or tablet. The device can include, for example, one or more of processors 802, input device 806, output device 808, storage 810, and communication device 804. Input device 806 and output device 808 can generally correspond to those described above and can either be connectable or integrated with the computer.

Input device 806 can be any suitable device that provides input, such as a touch screen, keyboard or keypad, mouse, or voice-recognition device. Output device 808 can be any suitable device that provides output, such as a touch screen, haptics device, or speaker.

Storage 810 can be any suitable device that provides storage, such as an electrical, magnetic, or optical memory, including a RAM, cache, hard drive, or removable storage disk. Communication device 804 can include any suitable device capable of transmitting and receiving signals over a network, such as a network interface chip or device. The components of the computer can be connected in any suitable manner, such as via a physical bus or wirelessly.

Software 812, which can be stored in storage 810 and executed by processor 802, can include, for example, the programming that embodies the functionality of the present disclosure (e.g., as embodied in the devices as described above).

Software 812 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 810, that can contain or store programming for use by or in connection with an instruction execution system, apparatus, or device.

Software 812 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Device 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 800 can implement any operating system suitable for operating on the network. Software 812 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

EXAMPLES

The application may be better understood by reference to the following non-limiting example, which is provided as an exemplary embodiment of the application. The following example is presented in order to more fully illustrate embodiments and should in no way be construed as limiting the broad scope of the application. While certain embodiments of the present application have been shown and described herein, it will be clear to one skilled in the art that such embodiments are provided by way of example only. Numerous variations, changes, and substitutions may occur to those skilled in the art without departing from the spirit and scope of the claims. It should be understood that various alternatives to the embodiments described herein may be employed in practicing the methods described herein.

Example 1. Biological Applications of the Provided Methods

This Example demonstrates a biological context for the provided method for determining a cell state of one or more cells or method for modeling disease progression, as described herein. In particular, this Example demonstrates an induced pluripotent stem cell (iPSC) derived motor neuron differentiation procedure which may be used for investigation of neurite growth an axonal transport.

Motor Neuron Differentiation from iPSCs

The motor neuron differentiation procedure was adapted from Fernandopulle et al. *Curr Protoc Cell Biol.* 2018 June; 79 (1): e51. Doxycycline inducible expression of three neuronal transcription factors ISL1, LHX3, and NGN2 in iPSC lines resulted in rapid and efficient motor neuron differentiation, which may be used to study axon degeneration and motor neuron diseases.

Briefly, iPSCs were cultured in TeSR™-E8™ culture medium on vitronectin coated plates, and passaged with ReLeSR™ (STEMCELL Technologies). PiggyBac™ based plasmid transfection was used to generate hNIL iPSC lines after G418 selection. To generate TDP43 wildtype and TDP43Δ NLS overexpressing iPSC lines, we PiggyBac™ plasmids encoding these constructs were transfected and iPSC cells were selected with Blasticidin. CRISPR-Cas9 gene editing to remove the G4C2 repeats from C9orf72 repeat expansion iPSC lines.

iPSCs were then differentiated into day 2 hNIL motor neuron progenitor cells. 6 well plates were coated with Matrigel® (Corning, #354277), and 70% iPSC cultures were dissociated into single cells with Accutase™ (STEMCELL Technologies, Cat #07920) and counted. 0.25-0.5 million cells were seeded in each well of the 6 well plates with E8™ medium supplemented with 1:5000 Rock inhibitor (Y27632, SelleckChem, S1049, in 50 mM stock solution). 24 hours post-seeding, cells were washed once with phosphate buffered saline (PBS) (Gibco) once and differentiated was induced with doxycycline induction medium (DMEM/F-12, 10 mM HEPES, 1× N2, 1× Non-essential amino acids, 1× Gluta-Max, 10 μM Rock inhibitor, 0.2 μM compound E, and 2 μM Doxycycline). 48 hours post doxycycline induction, the cells were treated with Accutase™ for 5 to 10 minutes at 37° C. The cells were then pipetted to remove cell clusters and transferred as single progenitor cells. Day 2 progenitor cells may be banked (2-3 million cells/vial) with CryoStor CS10 (Sigma-Aldrich).

Day 2 progenitor cells were then seeded in 96 well glass plates (96-1.5H-N) at about 20,000 cells/well or 12 well glass plates (P12-1.5H-N) at 200,000 cells/well. The plates were coated with PLO (Sigma P4957-50 mL) overnight at 37° C. The next day, PLO was removed and the plates were dried in a BSC hood for 3 hours. The plates were then coated with diluted Laminin-511 (5 μL/mL PBS dilution from stock Biogem, BG iMatrix-511). After 1 hour, NGN2 maintenance medium (Neurobasal Plus, 1× B27 plus, 1× Glutmax™, BDNF, 1 μg/mL, NT3, 1 μg/mL, and mouse Laminin 0.2 μg/mL; supplemented with 0.2 μM compound E, 2 μM Doxycycline, and 1 μg/mL EdU) was added for seeding. After 24 hours, the cells were washed with PBS once, and cultured in fresh NGN2 maintenance medium without compound E or Doxycycline. To complete motor neuron differentiation, the cells were feed ½ medium 3 times per week.

Imaging of the Cultured Motor Neurons

The resulting motor neurons are imaged using the provided methods. Briefly, live images are collected between differentiation days 3 to 40 of the above described protocol. Imaging timing may be optimized based on phenotype readouts.

Imaging may be used, for example, to determine a cell state. Alternatively, imaging may be used to generate a disease model for modeling the progression of the disease.

What is claimed is:

1. A system for determining a cell state of one or more cells, comprising:

one or more processors;

a memory; and one or more programs, wherein the one or more programs are stored in the memory and configured to be executed by the one or more processors, the one or more programs including instructions for:

receiving a set of time-series image data depicting one or more cells;

determining a sequence of embeddings by inputting the set of time-series image data into a first trained machine learning model;

determining a summary embedding based on the sequence of embeddings, the summary embedding comprising a temporal dimension based on temporal information associated with the sequence of embeddings; and determining the cell state of the one or more cells of the subject by inputting the summary embedding into a second trained machine learning model.

2. The system of claim 1, wherein the temporal information associated with the sequence of embeddings comprises at least one of:

a temporal relationship between a first embedding in the sequence of embeddings and a second embedding in the sequence of embeddings, a sequential relationship between a first embedding in the sequence of embeddings and a second embedding in the sequence of embeddings, and a time stamp associated with each embedding in the sequence of embeddings.

3. The system of claim 1, wherein the set of time-series image data comprises at least one of: a time series of images, a video segment, a plurality of fluorescence images, a plurality of phase images, and image data acquired at a frame rate of at least four frames per second.

4. The system of claim 3, wherein the plurality of phase images is captured using an imager with a frame rate of at least four frames per second.

5. The system of claim 4, wherein the frame rate is about 40 frames per second.

6. The system of claim 3, wherein the plurality of fluorescence images is captured using an imager with a frame rate of at least four frames per second.

7. The system of claim 6, wherein the one or more genetic mutations is selected from the group consisting of a deletion mutation, insertion mutation, substitution mutation, missense mutation, nonsense mutation, and frameshift mutation.

8. The system of claim 1, wherein the cell state is indicative of a diseased state, a healthy state, or a degree of the diseased state, and wherein the one or more programs include instructions for: determining, based on the cell state of the one or more cells and the set of time-series image data, a relationship between one or more time-variant morphological characteristics depicted in the set of time-series image data and the cell state of the one or more cells.

9. The system of claim 8, wherein the one or more programs include instructions for: determining, based on the cell state of the one or more cells and the set of time-series image data, a relationship between one or more subcellular or cellular movements or processes depicted in the set of time-series image data and the cell state of the one or more cells.

10. The system of claim 8, wherein the one or more live biological cells have a phenotypic difference compared to healthy cells that do not comprise the one or more genetic mutations, wherein the phenotypic difference comprises a difference in metabolic activity, cellular kinetics, cellular morphology, or any combination thereof.

11. The system of claim 1, wherein the cell state includes an indication of an accumulation of lipids.

12. The system of claim 1, wherein the cell state is indicative of at least one of: a level of metabolic activity and a kinetic state.

13. The system of claim 1, wherein a rate of change in the cell state is indicative of a variation of a cellular process, wherein the cellular process includes any one or more of a cargo transport, an organelle assembly, and an organelle disassembly.

14. The system of claim 1, wherein the one or more programs include instructions for mapping a network of one or both of axons and neurites to a cell of the one or more cells based on the set of time-series image data and the cell state of the one or more cells.

15. The system of claim 1, wherein the first machine learning model is pre-trained using unlabeled images that do not depict biological samples and retrained using unlabeled images of biological samples.

16. The system of claim 1, wherein determining the summary embedding based on the sequence of embeddings comprises: inputting the sequence of embeddings into a third trained machine learning model.

17. The system of claim 1, wherein the set of time-series image data depicts a single cell, wherein the single cell is identified using an image segmentation model.

18. The system of claim 1, wherein the one or more cells comprise one or more live biological cells, and wherein the one or more live biological cells comprise at least one of: one or more mammalian cells, one or more neurons, healthy cells, diseased cells, one or more genetic mutations, or any combination thereof.

19. A method for determining a cell state of one or more cells, the method comprising:

receiving a set of time-series image data depicting one or more cells;

determining a sequence of embeddings by inputting the set of time-series image data into a first trained machine learning model;

determining a summary embedding based on the sequence of embeddings, the summary embedding comprising a temporal dimension based on temporal information associated with the sequence of embeddings; and determining the cell state of the one or more cells of the subject by inputting the summary embedding into a second trained machine learning model.

20. A non-transitory computer-readable storage medium storing one or more programs for determining a cell state of one or more cells, the one or more programs comprising instructions, which when executed by one or more processors of an electronic device, cause the electronic device to:

receive a set of time-series image data depicting one or more cells;

determine a sequence of embeddings by inputting the set of time-series image data into a first trained machine learning model;

determine a summary embedding based on the sequence of embeddings, the summary embedding comprising a temporal dimension based on temporal information associated with the sequence of embeddings; and determine the cell state of the one or more cells of the subject by inputting the summary embedding into a second trained machine learning model.

* * * * *